US008853270B2

(12) United States Patent
Hadfield et al.

(10) Patent No.: US 8,853,270 B2
(45) Date of Patent: *Oct. 7, 2014

(54) SUBSTITUTED STILBENES AND THEIR REACTIONS

(75) Inventors: John Anthony Hadfield, Salford (GB); Alan Thomson McGown, Manchester (GB); Stephen Patrick Mayalarp, Manchester (GB); Edward John Land, Manchester (GB); Ian Hamblett, Bolton (GB); Keira Gaukroger, Hove (GB); Nicholas James Lawrence, Bristol (GB); Lucy Annette Hepworth, Cheshire (GB); John Butler, Salford (GB)

(73) Assignee: University of Salford, Salford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/588,331

(22) Filed: Aug. 17, 2012

(65) Prior Publication Data
US 2013/0023663 A1   Jan. 24, 2013

Related U.S. Application Data

(63) Continuation of application No. 11/744,405, filed on May 4, 2007, now abandoned, which is a continuation of application No. 10/451,213, filed as application No. PCT/GB01/05702 on Dec. 20, 2001, now Pat. No. 7,220,784.

(30) Foreign Application Priority Data

Dec. 21, 2000   (GB) .................................. 0031262.9
Jan. 5, 2001    (GB) .................................. 0100295.5

(51) Int. Cl.
```
C07C 229/00    (2006.01)
C07C 43/18     (2006.01)
A61K 31/225    (2006.01)
A61K 31/075    (2006.01)
C07C 205/37    (2006.01)
C07C 43/23     (2006.01)
C07C 205/35    (2006.01)
C07C 46/06     (2006.01)
C07C 43/215    (2006.01)
C07D 213/68    (2006.01)
C07F 7/18      (2006.01)
C07C 50/30     (2006.01)
C07C 205/44    (2006.01)
C07C 271/22    (2006.01)
```

(52) U.S. Cl.
CPC ............ *C07F 7/1852* (2013.01); *C07C 205/37* (2013.01); *C07C 43/23* (2013.01); *C07C 205/35* (2013.01); *C07C 46/06* (2013.01); *C07C 43/215* (2013.01); *C07D 213/68* (2013.01); *C07C 50/30* (2013.01); *C07C 205/44* (2013.01); *C07C 271/22* (2013.01)

USPC ............ 514/548; 514/720; 560/155; 568/631

(58) Field of Classification Search
None
See application file for complete search history.

(56) References Cited

U.S. PATENT DOCUMENTS

| 4,569,786 | A | 2/1986 | Deguchi |
| 4,996,237 | A | 2/1991 | Pettit et al. |
| 5,430,062 | A | 7/1995 | Cushman et al. |
| 5,561,122 | A | 10/1996 | Pettit |
| 7,220,784 | B2 * | 5/2007 | Hadfield et al. ............... 514/749 |

FOREIGN PATENT DOCUMENTS

| EP | 0 641 767 | 9/1994 |
| WO | 92/16486 | 10/1992 |
| WO | 99/35150 | 7/1999 |
| WO | 00/48590 | 8/2000 |
| WO | 01/12579 | 2/2001 |

OTHER PUBLICATIONS

Clark et al., STN Accession No. 1966:18865; Document No. 64:18865; abstract of Journal of the Chemical Society, Nov. 1965, 6509-6519.*

Pettit, G.R. et al., "Isolation and structure of the strong cell growth and tubulin inhibitor combretastatin A-4", Experientia, 45: 209-211 (1989).

(Continued)

*Primary Examiner* — Traviss C McIntosh, III
(74) *Attorney, Agent, or Firm* — Patrick J. Hagan; Dann, Dorfman, Herrell and Skillman, P.C.

(57) ABSTRACT

The present invention relates to stilbene and quinine compounds related to combretastatin A-4 and their use as anticancer compounds and prodrugs. The compounds include those with an alkyl group on the double bond of cis- or trans-stilbenes, compounds with one or more (and preferably 2 or 3) alkyl group substituents on the stilbene A ring, compounds with an alkoxy group other than methoxy at position 3, 4, and/or 5 of the stilbene A ring, compounds (or prodrugs) in which BBOC amino acid esters are formed with the phenolic hydroxyl at the 3-position of the B ring and compounds (or prodrugs) based on a benzoquinone B ring. The present invention further relates to the photochemical reactions of stilbene compounds, either the above compounds disclosed for the first time herein or compounds based on prior stilbenes. These reactions include the photochemical release of an active form of the compound from a prodrug conjugate and the photochemical isomerization of the compounds, especially from a trans to cis form of compounds. The reactions can be used alone or in combination to convert inactive or comparatively less active forms of the compounds to more active forms, thereby allowing the compounds to be selectively targeted, e.g., activating them at the site of a tumor.

21 Claims, 2 Drawing Sheets

(56) References Cited

OTHER PUBLICATIONS

Lin, C.M. et al., "Interactions of Tubulin with Potent Natural and Synthetic Analogs of the Antimitotic Agent Combretastatin: a Structure-Activity Study", Mol. Pharmacol., 34: 200-208 (1988).

Grosios, K. et al., "In vivo and in vitro evaluation of combretastatin A-4 and its sodium phosphate prodrug", British J. of Cancer, 81(8): 1318-1327 (1999).

Lin, C.M. et al., "Antimitotic Natural Products Combretastatin A-4 and Combretastatin A-2: Studies on the Mechanism of Their Inhibition of the Binding of Colchicine to Tubulin", Biochemistry, 28: 6984-6991 (1989).

Woods, J.A. et al., "The Interaction with tubulin of a series of stilbenes based on combretastatin A-4", British Journal of Cancer, 71: 705-711 (1995).

McGown, A.T. et al., "Differential cytotoxicity of Combretastatins A4 and A4 in two daunorubicin-resistant P388 cell lines", Cancer Chemother. Pharmacol., 26: 79-81 (1990).

El-Zayat, A.A.E. et al., "In vitro evaluation of the antineoplastic activity of combretastatin A-4, a natural product from *Combretum caffrum* (arid shrub)", Anti-Cancer Drugs, 4: 19-25 (1993).

Dark, G.G. et al., "Combretastatin A-4, an Agent That Displays Potent and Selective Toxicity Toward Tumor Vasculature", Cancer Research, 57: 1829-1834 (1997).

Brown, R.T. et al., "Synthesis of Water-soluble Sugar Derivatives of Combretastatin A-4", J. Chem. Soc. Prekin. Trans., 1: 577-581 (1995).

Pettit, G.R. et al., "Antineoplastic agents 322. Synthesis of combretastatin A-4 prodrugs", Anti-Cancer Drug Design, 10: 299-309 (1995).

Ducki, S. et al., "Potent Antimitotic and Cell Growth Inhibitory Properties of Substituted Chalcones", Bioorganic & Medicinal Chemistry Letters, 8: 1051-1056 (1998).

Zhao, S. et al., "Positron emission of tomography of murine liver metastases and the effects of treatment by combretastatin A-4", European Journal of Nuclear Medicine, 26: 231-238 (1999).

Aleksandrzak, K. et al., "Antimiotic activity of diaryl compounds with structural features resembling combretastatin A-4", Anti-Cancer Drugs, 9: 545-550 (1998).

Holmes, C.P., "Model Studies for New o-Nitrobenzyl Photolabile Linkers: Substituent Effects on the Rates of Photochemical Cleavage", J. Org. Chem., 62: 2370-2380 (1997).

Pettit, G.R. et al., "Antineoplastic Agents. 291. Isolation and Synthesis of Combretastatins A-4, A-5, and A-6", J. Med. Chem., 38: 1666-1672 (1995).

Irngartinger, H. et al., "Synthesis, Structures and Topochemistry of 2-Monovinyl-Substituted 1,4-Bezoquinones", Eur. J. Org. Chem., p. 605-626 (1998).

Sisido, K. et al., "The Preparation of Synthetic Estrogens. IV. Condensation of Biacetyl with Phenols", J. American Chemical Society, 71: 2037-2041 (1949).

Pinney, K.G. et al., "Synthesis and Biological Evaluation of Aryl Azide Derivatives of Combretastatin A-4 as Molecular Probes for Tubulin", Bioorganic & Medicinal Chemistry, 8: 2417-2425 (2000).

Pettit, G.R. et al., "Antineoplastic agents 429. Syntheses of the combretastatin A-4 and combretastatin B-1 prodrugs", Anti-Cancer Drug Design, 15: 203-216 (2000).

Lin et al., Molecular Pharmacology, 34: 200-208 (1988).

Badjic et al., "Unexpected Interactions between Sol-Gel Silica Glass and Guest Molecules. Extraction of Aromatic Hydrocarbons into Polar Silica from Hydrophobic Solvents", J. of Phys. Chem. B, 104(47): 11081-11087 (2000).

Clark, E., "Nuclear methylated diethylstilbestrols as possible anti-estrogens", J. Chem. Soc., 6509-19 (1965 [CAPLUS Abstract}.

Clark, E., "Estrogenic and anti-estrogenic properties of ring methyl-substituted stilbestrols", J. Pharmacy and Pharmacology, 23(5): 339-44 (1971) [CAPLUS Abstract].

\* cited by examiner

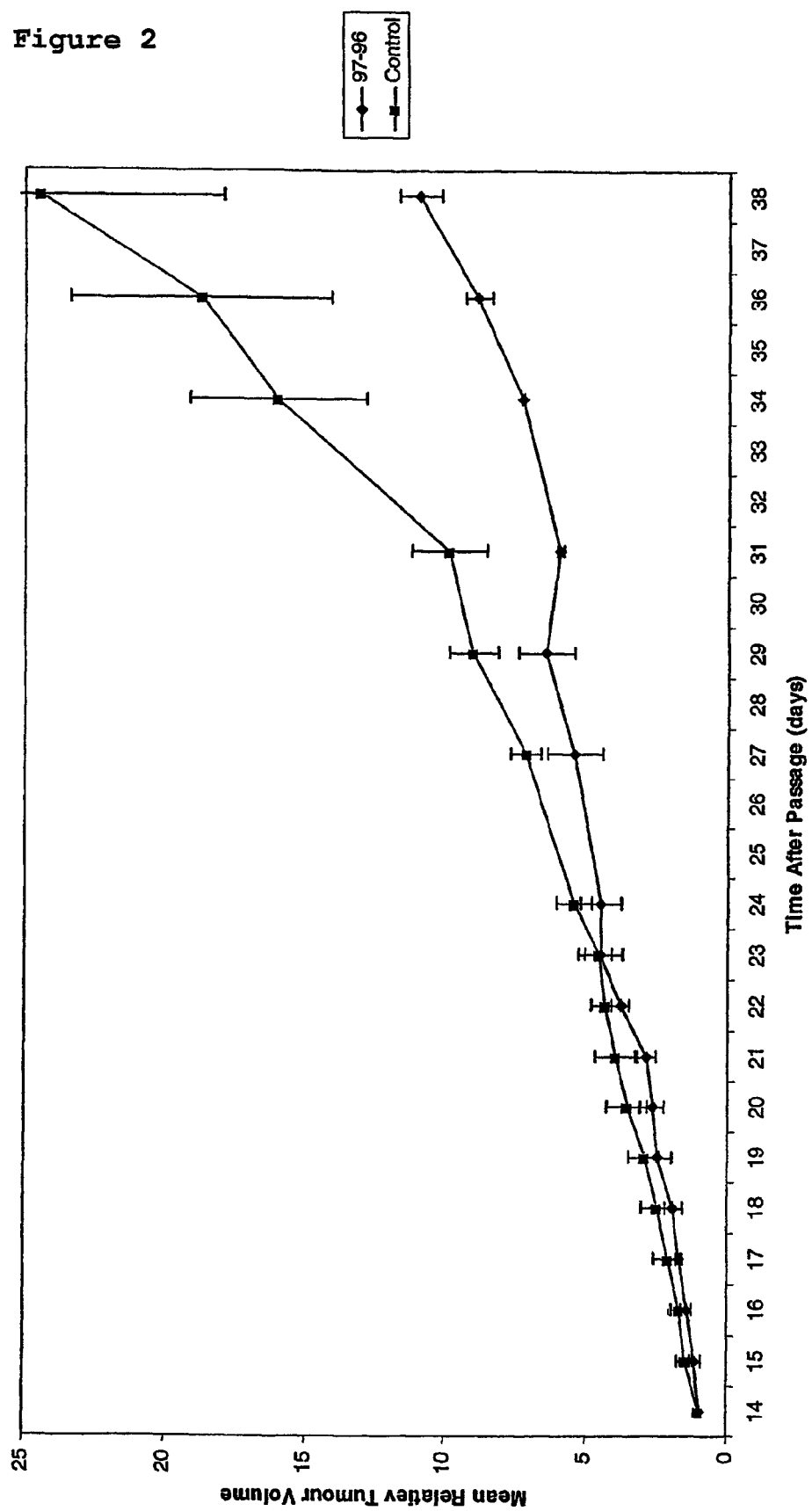

SUBSTITUTED STILBENES AND THEIR REACTIONS

CROSS-REFERENCE TO RELATED APPLICATIONS

This application is a continuation of U.S. patent application Ser. No. 11/744,405, filed May 4, 2007, which is a continuation of U.S. patent application Ser. No. 10/451,213, filed Mar. 3, 2004 (now U.S. Pat. No. 7,220,784, issued May 22, 2007), which is the U.S. National Stage of International Application No. PCT/GB01/05702, filed Dec. 20, 2001. The disclosures of the aforesaid applications are incorporated by reference in their entireties in the present application.

FIELD OF THE INVENTION

The present invention relates to novel compounds, and more particularly to stilbene and quinone compounds related to combretastatin A-4 and their possible use as anticancer compounds and prodrugs. In further aspects, the present invention relates to the photochemical reactions of some of these compounds, in the photochemical isomerisation of the compounds and/or the photochemical release of an active compound from a protected compound (prodrug).

BACKGROUND OF THE INVENTION

The stilbene cis-combretastatin A-4 Z-1, isolated from the African bush willow, *Combretum caffrum* shows exciting potential as an anticancer agent, binding strongly to tubulin and displaying potent and selective toxicity toward tumour vasculature (U.S. Pat. No. 4,996,237, Arizona Board of Regents, Pettit et al, *Experimentia*, 1989, 45, 209; Lin et al, *Mol. Pharmacol.*, 1988, 34, 200; Grosios et al, *Brit. J. Cancer*, 1999, 81, 1318; Lin et al, *Biochemistry*, 1989, 28, 6984; Woods et al, *Brit. J. Cancer*, 1995, 71, 705; McGown et al, *Cancer Chemother. Pharmacol.*, 1990, 26, 79; El-Zayat et al, *Anti-Cancer Drugs*, 1993, 4, 19; Dark et al, *Cancer Research*, 1997, 57, 1829.).

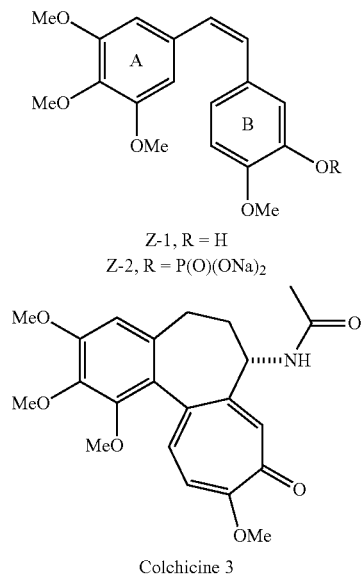

Z-1, R = H
Z-2, R = P(O)(ONa)$_2$

Colchicine 3

Cis-combretastatin A-4 Z-1 is able to inhibit cell growth at low concentrations (IC$_{50}$, P388 murine leukaemia cell line 2.6 nM). The potency of trans-combretastatin A-4 E-1 is much lower and inhibits cell growth in the μM range. Arguably, it is the ability of Z-1 and Z-2 to destroy tumour blood vessels, effectively starving tumours of nutrients, which makes them such exciting molecules. Tumour vasculature and the formation of neovasculature were first identified as a target for cancer therapy by Judah Folkman some 30 years ago. The work of Folkman and others has clearly identified angiogenesis and blood supply as necessary requirements for primary tumour growth, invasiveness and metastasis. It is now becoming clear that the selective destruction of tumour vasculature will have a significant impact on the clinical treatment of cancer. Angiogenesis is subject to a complex process of regulation and thereby offers a multitude of molecular targets for drug design.

The use of Z-1 as a clinically useful anticancer agent has been severely hampered by its poor water solubility (Brown et al, *J. Chem. Soc., Perkin Trans.* 1, 1995, 577). The phosphate salt Z-2 is more soluble in water than Z-1 and is soon to enter phase II clinical trials (Pettit et al, *Anti-Cancer Drug Des.*, 1995, 10, 299). Nevertheless, both Z-1 and Z-2 are not targeted towards cancer cells and their therapeutic efficacy would be improved if their selectivity were better. The low solubility of cis-combretastatin A-4 in water and saline has led to attempts in the art to make related compounds or prodrugs which retain the activity of cis-combretastatin A-4 as an anticancer agent and which have enhanced solubility. These attempts focus on forming salts or derivatives at the phenolic hydroxyl group of combretastatin. By way of example, U.S. Pat. No. 5,561,122 (Arizona Board of Regents) discloses the sodium and potassium salts of cis-combretastatin A-4 and a hemisuccinic acid ester derivative, and WO99/35150 (Arizona Board of Regents) discloses the lithium, caesium, magnesium, calcium, manganese and zinc salts of cis-combretastatin A-4, and ammonium cation salts with imidazole, morpholine, piperazine, piperidine, pyrazole, pyridine, adenosine, cinchonine, glucosamine, quinine, quinidine, tetracycline and verapamil.

At the molecular level, both compounds target tubulin, binding strongly at or close to the colchicine (3) binding site, preventing polymerisation of α,β-tubulin heterodimer to microtubules. Their inhibition of microtubule formation prevents mitosis and is important in disrupting the growth of new vascular epithelial cells. In addition, disruption of the intracellular microtubule networks by combretastatin A4 leads to the destruction of microvessels within the tumour. This antivascular activity offers exciting therapeutic possibilities as the destruction of microvessels results in the death of all tumour cells which depend on the vessel for nutrients and oxygen. The multi-functional role of tubulin in both healthy and cancer cells highlights the need for selectively targeted drugs.

We have previously investigated the tubulin-binding properties of agents related to Z-1 and 3 and as part of this effort, we have designed many related compounds that behave in a similar fashion to Z-1 (Ducki et al, *Bioorg. Med. Chem. Lett.*, 1998, 8, 1051; Zhao et al, *Eur. J. Nuc. Medicine*, 1999, 26, 231; Aleksandrzak et al, *Anti-Cancer Drugs*, 1998, 9, 545). However, it remains a problem in the art in designing effective compounds and especially those which can be selectively targeted.

SUMMARY OF THE INVENTION

In a first group of aspects, the present invention relates to novel compounds and more particularly to stilbene and quinone compounds related to combretastatin A-4. The synthesis of new compounds is disclosed herein, together with experiments demonstrating their activity in vitro and in vivo, supporting their use as anticancer compounds and prodrugs. The compounds include those with an alkyl group on the double bond of cis or trans-stilbenes, compounds with one or more (and preferably 2 or 3) alkyl group substituents on the stilbene A ring, compounds with an alkoxy group other than methoxy at position 3, 4, and/or 5 of the stilbene A ring, compounds (or prodrugs) in which BOC amino acid esters are formed with the phenolic hydroxyl at the 3-position of the B ring and compounds (or prodrugs) based on a benzoquinone B ring.

In a further group of aspects, the present invention relates to the photochemical reactions of stilbene compounds, either the above compounds disclosed for the first time herein or compounds based on prior art stilbenes. These reactions include the photochemical release of an active form of the compound from a prodrug conjugate and the photochemical isomerisation of the compounds, especially from a trans to cis form of compounds. The reactions can be used alone or in combination to convert inactive or comparatively less active forms of the compounds to more active forms, thereby allowing the compounds to be selectively targeted, e.g. activating them at the site of a tumour.

Accordingly, in a first aspect, the present invention provides a compound represented by the structural formula:

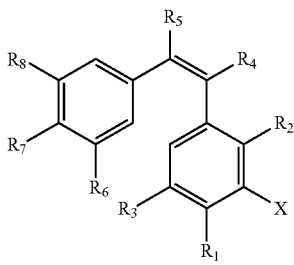

wherein:
X is selected from hydroxyl, nitro, amino, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl or O-ester;
$R_1$ is selected from alkyl, CHO, alkoxy, $NH_2$, NHR, NRR', SR, $CF_3$ or halogen;
$R_2$ and $R_3$ are independently selected from hydrogen, alkyl, alkoxy, hydroxyl $NH_2$, NHR, NRR', SR, haloalkyl or halogen;
$R_4$ and $R_5$ are independently selected from hydrogen, alkyl, $CH_2NHCOR''$ or $CH_2CONHR''$; and,
$R_6$, $R_7$ and $R_8$ are independently selected from hydrogen, alkyl or alkoxy;
or a salt or derivative thereof.

In all aspect of the invention, preferably, the substituents are chosen according to the following lists of preferred groups.

Preferably, alkyl or alkoxy substituents are substituted or unsubstituted $C_{1-10}$ alkyl or alkoxy groups. In either case, the alkyl chain can be straight chain or branched.

Preferred alkyl substituents are methyl or ethyl. Preferred alkoxy substituents are methoxy or ethoxy.

Halogen substituents can be fluorine, chlorine, bromine or iodine, and are preferably fluorine. Preferably, the haloalkyl groups are fluoroalkyl, and most preferably is a $CF_3$ group.

Preferably, the O-ester group is represented by the formula O-phosphate, OCO-alkyl, OCO-aryl, OCO-heteroaryl, OCO-amino acid, OCO-peptide, OCO-polymer, OCO-sugar or OCO—CHR—NH—BOC, where BOC represents a t-butoxycarbonyl group.

As used herein, preferably R and R' are substituted or unsubstituted $C_{1-10}$ alkyl groups. R" is preferably selected from substituted or unsubstituted alkyl (e.g. $C_{1-10}$), aryl or heteroaryl groups.

In a further aspect, the present invention provides compounds in which there are one or more alkyl groups present on the double bond linking the stilbene A and B rings. Thus, in this aspect, the present invention provides compounds represented by the structural formula:

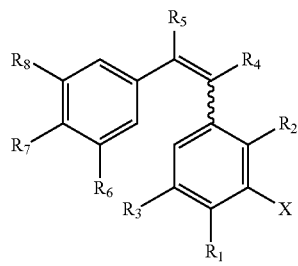

wherein:
the zigzag line indicates that the compound can be cis or trans;
X is selected from hydroxyl, nitro, amino, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl or O-ester;
$R_1$ is selected from alkyl, CHO, alkoxy, $NH_2$, NHR, NRR', S, $CF_3$ or halogen;
$R_2$ and $R_3$ are independently selected from hydrogen, alkyl, alkoxy, hydroxyl, $NH_2$, NHR, NRR', SR, haloalkyl or halogen;
$R_4$ and $R_5$ are independently selected from hydrogen, alkyl, $CH_2NHCOR''$ or $CH_2CONHR''$; and,
$R_6$, $R_7$ and $R_8$ are independently selected from hydrogen, alkyl or alkoxy;
wherein at least one of the substituents $R_4$ and $R_5$ is an alkyl group.
or a salt or derivative thereof.

As defined above, the compounds in this aspect of the invention may be either the cis or Z-isomer, i.e. be related to combretastatin A4, or the trans or E-isomer. Examples of the synthesis of both isomers are proved below. Preferably, the alkyl group $R_4$ and/or $R_5$ is a methyl or ethyl group.

In a further aspect, the present invention provides compounds in which one or more of the methoxy groups on the A ring of combretastatin is replaced by an alkyl group. Thus, in this aspect, the present invention provides compounds represented by the structural formula:

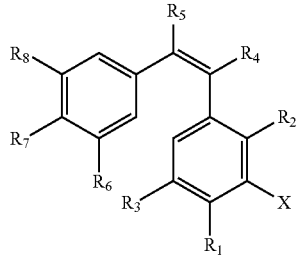

wherein:
X is selected from hydroxyl, nitro, amino, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl or O-ester;

$R_1$ is selected from alkyl, CHO, alkoxy, $NH_2$, NHR, NRR', SR, $CF_3$ or halogen;

$R_2$ and $R_3$ are independently selected from hydrogen, alkyl, alkoxy, hydroxyl, $NH_2$, NHR, NRR', SR, haloalkyl or halogen;

$R_4$ and $R_5$ are independently selected from hydrogen, alkyl, $CH_2NHCOR''$ or $CH_2CONHR''$; and, wherein $R_6$, $R_7$ and $R_8$ are independently selected from hydrogen, alkyl or alkoxy such that at least one of these substituents is an alkyl group;

or a salt or derivative thereof.

In preferred embodiment, two or more preferably all three of the groups are alkyl groups. Exemplary compounds include those with methyl, ethyl or propyl groups. In a preferred embodiment, $R_6$, $R_7$ and $R_8$ are methyl groups.

In a further aspect, the present invention provides compounds in which one or more of the methoxy groups on the A ring of combretastatin is replaced by a higher alkoxy group, i.e. an ethoxy or longer chain group. Thus, in this aspect, the present invention provides compounds represented by the structural formula:

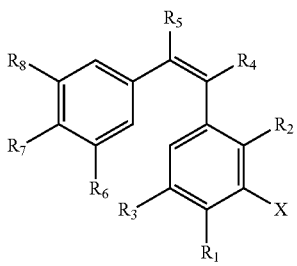

wherein:
X is selected from hydroxyl, nitro, amino, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl, or O-ester;

$R_1$ is selected from alkyl, CHO, alkoxy, $NH_2$, NHR, NRR', SR, $CF_3$ or halogen;

$R_2$ and $R_3$ are independently selected from hydrogen, alkyl, alkoxy, hydroxyl, $NH_2$, NHR, NRR', SR, haloalkyl or halogen;

$R_4$ and $R_5$ are independently selected from hydrogen, alkyl, $CH_2NHCOR''$ or $CH_2CONHR''$; and, wherein $R_6$, $R_7$ and $R_8$ are independently selected from hydrogen, alkyl or alkoxy such that at least one of these substituents is an alkoxy group other than methoxy group;

or a salt or derivative thereof.

Preferably, two or all three of the groups is replaced by an alkoxy group other than methoxy.

In a further aspect, the present invention relates to compounds in which the phenolic hydroxyl group on the B ring of the combretastatin is derivatised to form a t-BOC-amino acid ester. These compounds may be prodrugs capable of releasing combretastatin, or a variant thereof, e.g by the action of an enzyme capable of hydrolysing the BOC-amino acid ester, e.g. an esterase enzyme. Thus, in this aspect, the present invention provides compounds represented by the structural formula:

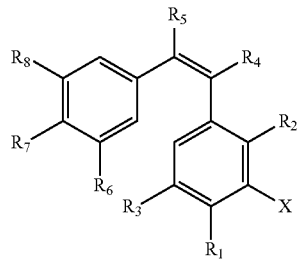

wherein:
$R_1$ is selected from alkyl, alkoxy, $NH_2$, NHR, NRR', SR, $CF_3$, CHO or halogen;

$R_2$ and $R_3$ are independently selected from hydrogen, alkyl, alkoxy, hydroxyl, $NH_2$, NHR, NRR', SR, haloalkyl or halogen;

$R_4$ and $R_5$ are independently selected from hydrogen, alkyl, $CH_2NHCOR''$ or $CH_2CONHR''$; and, $R_6$, $R_7$ and $R_8$ are independently selected from hydrogen, alkyl or alkoxy; and, or a salt or derivative thereof;

wherein X is a group represented by:

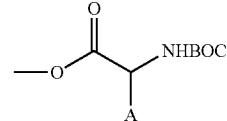

wherein BOC represents a t-butoxycarbonyl group and the A group is an amino acid side chain.

The BOC amino acid ester may include a naturally occurring or synthetic amino acid, in either the D or L-isoform. Examples of compounds of the aspect of the invention include those where the amino acid is Phe, Ile, Gly, Trp, Met, Leu, Ala, His, Pro, D-Met, D-Trp, or Tyr, e.g. when in compound 33 the amino acid is Phe, the A group is —$CH_2$Ph etc.

In a further aspect, the present invention provides compounds in which the B ring of combretastatin is replaced by a substituted or unsubstituted benzoquinone ring. These quinone compounds may act as prodrugs of combretastatin and be activated in vivo by enzymes such as DT-diaphorase. Thus, in this aspect, the present invention provides compounds represented by the structural formula:

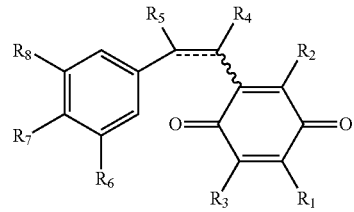

wherein:
the dotted line indicates a single or double covalent bond and the zigzag line indicates that the compound can be cis or trans;

$R_1$, $R_2$ and $R_3$ are independently selected from hydrogen, alkyl, CHO, COR, alkoxy, hydroxyl, $NH_2$, NHR, NRR', SR, haloalkyl or halogen;

$R_4$ and $R_5$ are independently selected from hydrogen, alkyl, $CH_2NHCOR''$ or $CH_2CONHR''$; and, $R_6$, $R_7$ and $R_8$ are independently selected from hydrogen, alkyl or alkoxy; or a salt or derivative thereof.

The present invention also includes compositions comprising one or more of the above defined compounds. In other aspects, the present invention provides the compounds for use in a method of medical treatment and the use of the compounds for the preparation of a medicament for the treatment of a condition that responds to the medicament, and in particular for the treatment of cancer. The compounds may act directly or be prodrugs capable of releasing an active form of the compound upon hydrolysis or reduction, e.g. as mediated in situ by an enzyme.

In the second group of aspects, the present invention provides a prodrug comprising a compound conjugated to a photocleavable group, wherein the prodrug is represented by the general formula:

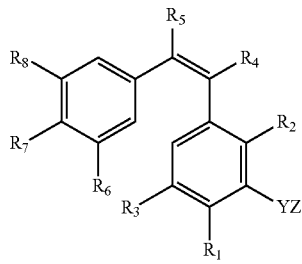

wherein:

$R_1$ is selected from alkyl, CHO, alkoxy, $NH_2$, NHR, NRR', SR, $CF_3$ or halogen;

$R_2$ and $R_3$ are independently selected from hydrogen, alkyl, alkoxy, hydroxyl, $NH_2$, NHR, NRR', SR, haloalkyl or halogen;

$R_4$ and $R_5$ are independently selected from hydrogen, alkyl, $CH_2NHCOR''$ or $CH_2CONHR''$; and, $R_6$, $R_7$ and $R_8$ are independently selected from hydrogen, alkyl or alkyoxy;

Y is selected from O, S, Se, NH; and,

Z is a photocleavable group;

or a salt or derivative thereof.

The compounds conjugated to the photocleavable group to form the prodrug may be the new combretastatin derivatives disclosed herein or may be a known combretastatin which has not be conjugated in this way in the prior art.

The prodrugs can be activated by exposure to electromagnetic radiation, especially ultraviolet-visible light (e.g. having a wavelength of between about 190-1000 nm), to remove the protecting photocleavable group and cause the release of the compound. Thus, the prodrugs can be used to provide selective activation of the active form of the compound, e.g. at the site of a tumour, by administering the compound and exposing to light the site at which activation is required.

Particularly preferred compounds (prodrugs) are those which can be exposed to light to release combretastatin, and especially cis-combretastatin A4.

Examples of preferred compounds include those which Z, the photocleavable group is selected from:

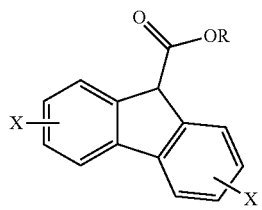

D. H. R Barton, Y. L. Chow, A. Cox, and G. W. Kirby, *J. Chem. Soc.*, 1965, 3571.

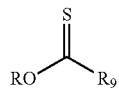

T. Kishi, T. Tsuchiya and S. Umezawa, *Bull. Chem. Soc. Jpn.*, 1979, 52, 3015.

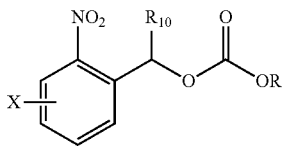

L. D. Cama and B. G. Christensen, *J. Am. Chem. Soc.*, 1978, 100, 8006.

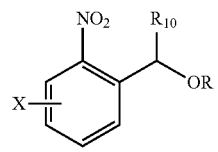

Patchornik, A.; Amit, B.; Woodward R. B. *J. Am. Chem. Soc.*, 1970, 92, 6333-6335

B. Amit, E. Hazum, M. Fridkin, and A. Patchornik, *Int. J. Pept. Protein Res.*, 1977, 9, 91.

In the above formulae, R is the photoprotected group, $R_9$ and $R_{10}$ are independently selected from alkyl, aryl or heteroaryl and X is any functional group. Examples of photoactivatable groups are also provided on pages 54-59.

In a further aspect, the present invention provides the compounds as defined herein for use in a method of medical treatment. In preferred embodiments, the present invention provides the use of the compounds defined herein for the preparation of a medicament for the treatment of a condition that is ameliorated by administration of the activated or released form of the compound. In such uses, it is preferred that the activated form of the compound has significantly greater activity than the protected form of the compound, e.g. making it possible to obtain selectivity in the delivery and activation of the compound, e.g. to a target tissue. In preferred embodiments of the invention, the compounds are employed in medicaments for the treatment of cancer.

In a further aspect, the present invention provides a process for providing the compound at a site, the process comprising exposing a prodrug represented by the above formula to light to release the compound at the site. In this embodiment of the invention, preferably the light is in the visible range, e.g. from about 350-800 nm.

In a further aspect, the present invention provides a process for isomerising a compound represented by the general formula:

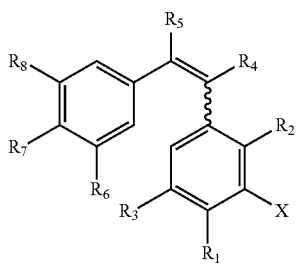

wherein:
- $R_1$ is selected from alkyl, alkoxy, CHO, $NH_2$, NHR, NRR', SR, $CF_3$ or halogen;
- $R_2$ and $R_3$ are independently selected from hydrogen, alkyl, alkoxy, hydroxyl, $NH_2$, NHR, NRR', SR, haloalkyl or halogen;
- $R_4$ and $R_5$ are independently selected from hydrogen, alkyl, $CH_2NHCOR''$ or $CH_2CONHR''$; and,
- $R_6$, $R_7$ and $R_8$ are independently selected from hydrogen, alkyl or alkoxy;
- X is selected from hydroxyl, nitro, amino, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl, O-ester, or the group Y—Z as defined above;
- or a salt or derivative thereof;
- the process comprising exposing the compound to light so that it isomerises from the E-isomer to the Z-isomer. This process might be carried out separately or in conjunction with the light activated release of the compound from a prodrug as defined above.

In a further aspect, the present invention provides a process for producing the photoactivatable compounds defined herein, the process comprising linking a photoactivatable group to the Y group of a precursor compound to produce photoactivatable compounds as defined above.

The work disclosed herein arises from the findings that the inactive trans isomer of combretastatin A-4 E-1 can be converted to the active cis-isomer Z-1 by the action of ultraviolet light ex situ in a photochemical reactor. The irradiation of E-1 in this manner leads to an impressive and rapid increase in activity. Further we have found that only after a long period of irradiation is the formation of the phenanthrene (which is only moderately active, as measured by its ability to inhibit cancer cell growth in vitro, $IC_{50}$ 0.7 μM) evident. We have prepared phenanthrene, by irradiation of E-1, in good yield when an oxidant ($I_2$) is present (to oxidize the first-formed cyclization product). This provides an opportunity to exploit the hypoxic nature of solid tumours and increase the selectivity of irradiated E-1. In other words, healthy cells may provide an oxidative pathway for the formation of the less toxic phenanthrene and effectively decrease the lifetime of Z-1.

The same result can be achieved in situ in the presence of cultured cancer cells (K562 human myelogenous leukaemia cell line). These experiments showed that within 2 seconds of exposure to ultraviolet light the activity of the E-combretastatin A-4 ($IC_{50}$ originally 5 μM) increases to 2 nM, providing a rapid thousand-fold increase in activity. Moreover, the cells in the absence of the drug are not affected by exposure to the radiation and grow normally over the 5 days of the assay. To increase the water solubility of the drug we have produced prodrugs with a photo-cleavable group attached to the B-ring phenolic OH group. The nitro vanillin derivative was chosen since it has been used as a photo-cleavable linker for solid phase synthesis applications and its synthesis is relatively simple. These prodrugs have been successfully cleaved in both the E and Z series (E-6 and Z-6 respectively) and have produced highly cytotoxic agents in vitro upon in situ exposure to ultra violet radiation. The cleavage of the water solubilising group appears to be faster than the E→Z isomerisation, at least under ex situ irradiation. Thus, the use of Z-6 has some merit. Indeed it forms the prototype for systems that do not rely on any special photochemical features of the molecule to be delivered. This provides a more general approach to the site-specific photochemical activation of prodrugs. Moreover, the photocleavable water solubilising group can be engineered, so that cleavage occurs at longer wavelength and rapidly.

Embodiments of the present invention will now be described by way of example and not limitation with reference to the accompanying figures.

BRIEF DESCRIPTION OF THE FIGURES

FIG. 2 shows the anti-tumour activity of compound 97-96 in an in vivo tumour implant experiment in mice.

DETAILED DESCRIPTION

Pharmaceutical Compositions

Figure 1:
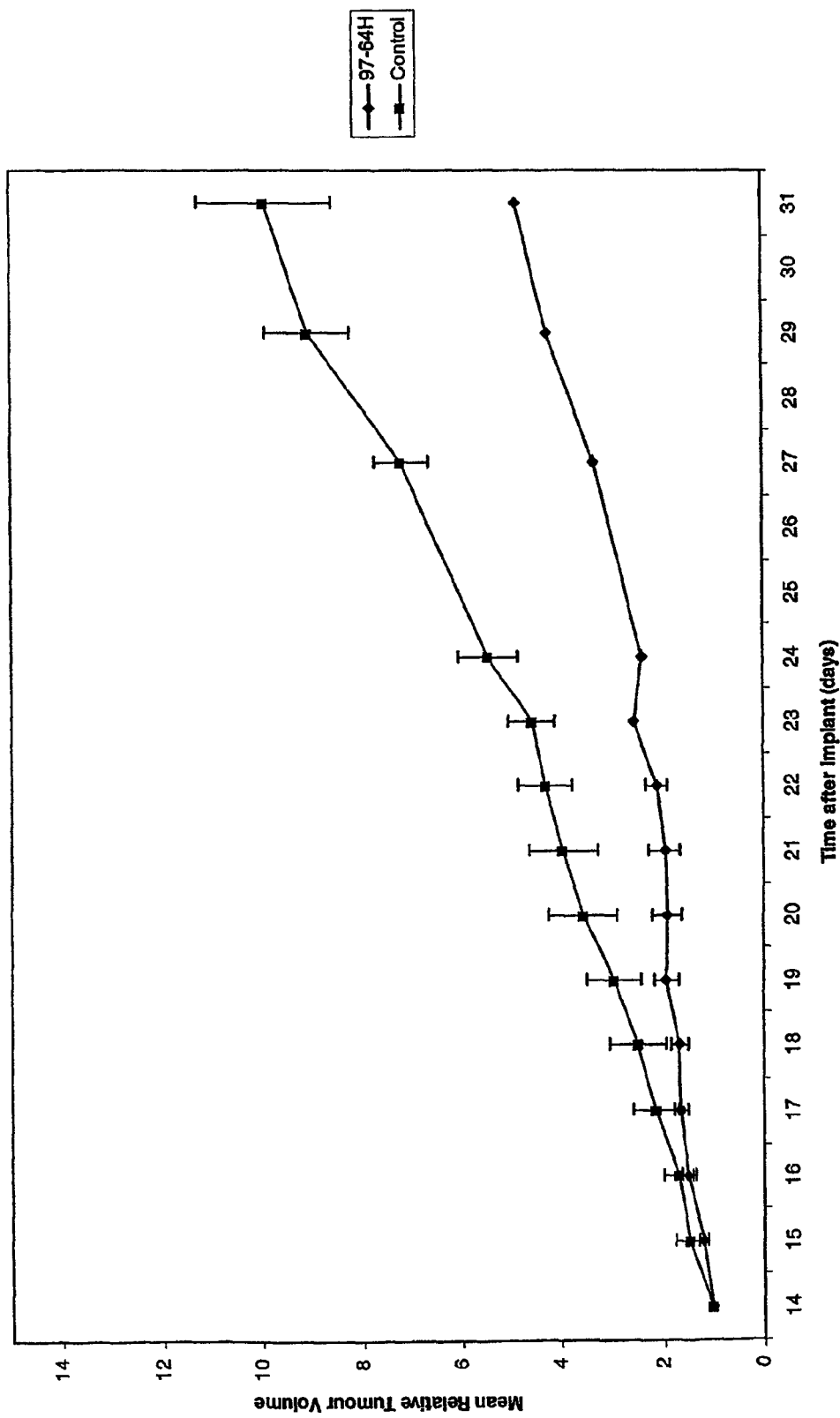
FIG. 1 shows the anti-tumour activity of compound 97-64H in an in vivo tumour implant experiment in mice.

The compounds of the invention may be derivatised in various ways. As used herein "derivatives" of the compounds includes salts, esters such as in vivo hydrolysable esters, free acids or bases, hydrates, prodrugs or coupling partners. In the case of compounds which are combretastatin or analogues thereof, preferably the derivatives are soluble in water and/or saline or can be hydrolysed to provide physiologically active agents.

Examples in the prior art of salts or prodrugs of cis-combretastatin A-4 focus on forming salts or derivatives at the phenolic hydroxyl group of combretastatin. These include sodium phosphate salts, sodium and potassium salts (U.S. Pat. No. 5,561,122), lithium, caesium, magnesium, calcium, manganese and zinc salts of cis-combretastatin A-4, and ammonium cation salts with imidazole, morpholine, piperazine, piperidine, pyrazole, pyridine, adenosine, cinchonine, glucosamine, quinine, quinidine, tetracycline and verapamil (WO99/35150).

Salts of the compounds of the invention are preferably physiologically well tolerated and non toxic. Many examples of salts are known to those skilled in the art. Compounds having acidic groups, can form salts with alkaline or alkaline earth metals such as Na, K, Mg and Ca, and with organic amines such as triethylamine and Tris(2-hydroxyethyl) amine. Salts can be formed between compounds with basic groups, e.g. amines, with inorganic acids such as hydrochloric acid, phosphoric acid or sulfuric acid, or organic acids such as acetic acid, citric acid, benzoic acid, fumaric acid, or tartaric acid. Compounds having both acidic and basic groups can form internal salts.

Esters can be formed between hydroxyl or carboxylic acid groups present in the compound and an appropriate carboxylic acid or alcohol reaction partner, using techniques well known in the art. Examples of esters include those formed between the phenolic hydroxyl of the substituted stilbenes and carboxylic acids, hemisuccinic acid esters, phosphate esters, BOC esters, sulphate esters and selenate esters.

Derivatives which as prodrugs of the compounds are convertible in vivo or in vitro into one of the parent compounds. Typically, at least one of the biological activities of compound will be reduced in the prodrug form of the compound, and can be activated by conversion of the prodrug to release the compound or a metabolite of it. Example of prodrugs include combretastatin A1 phosphate, combretastatin A4 phosphate and RH1.

Other derivatives include coupling partners of the compounds in which the compounds is linked to a coupling partner, e.g. by being chemically coupled to the compound or physically associated with it. Examples of coupling partners include a label or reporter molecule, a supporting substrate, a carrier or transport molecule, an effector, a drug, an antibody or an inhibitor. Coupling partners can be covalently linked to compounds of the invention via an appropriate functional group on the compound such as a hydroxyl group, a carboxyl group or an amino group.

The compounds described herein or their derivatives can be formulated in pharmaceutical compositions, and administered to patients in a variety of forms, in particular to treat conditions which are ameliorated by the activation of the compound.

Pharmaceutical compositions for oral administration may be in tablet, capsule, powder, cream, liquid form or encapsulated by liposomes. A tablet may include a solid carrier such as gelatin or an adjuvant or an inert diluent. Liquid pharmaceutical compositions generally include a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

Parental administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes. For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicizing agent, preservative or anti-oxidant or other materials well known to those skilled in the art. Such materials should be non-toxic and should not interfere with the efficacy of the active ingredient. The precise nature of the carrier or other material may depend on the route of administration, e.g. orally or parentally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutical compositions are given to an individual in a "prophylactically effective amount" or a "therapeutically effective amount" (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. By way of example, and the compositions are preferably administered to patients in dosages of between about 0.01 and 100 mg of active compound per kg of body weight, and more preferably between about 0.5 and 10 mg/kg of body weight. The compounds may be used in the treatment of cancer and other conditions involving abnormal proliferation of vasculature including diabetic retinopathy, psoriasis and endometriosis.

General

Proton nuclear magnetic resonance ($^1$H NMR) spectra were recorded on a Brüker AC 300 (300 MHz) or AC 400 (400 MHz) NMR spectrometer. Chemical shifts, δ, for all NMR spectra are given in ppm, relative to tetramethylsilane, and, unless otherwise stated, using $CDCl_3$ as both solvent and internal standard. Coupling constants (J) were measured in Hz. Melting points were determined on a Gallenkamp melting point apparatus and are uncorrected. The UV/VIS spectra were determined using a Hewlett-Packard HP8452 diode-array spectrophotometer. Extinction coefficients (a) are presented as their natural logarithms. Microanalyses were carried out by the laboratories of the Departments of Chemistry of the University of Manchester and UMIST. High resolution mass spectroscopy was determined using a Kratos Concept mass spectrometer. Thin layer chromatography (tlc) was performed using precoated aluminium-backed silica gel plates (60 $F_{254}$) with 0.2 mm thickness (Merck), with observation under UV when necessary. Gas chromatography was carried out using an SE 54 column at 195-225 kPa at 1.5 kPa/min. The oven temperature was 180-280° C. at 5° C./min.

Example 1

Synthesis of Combretastatins with Alkyl Groups on the Double Bond

Z- and E-1-(3'-t-Butyldimethylsilyloxy-4'-methoxyphenyl)-2-(3",4",5"-trimethoxyphenyl)propene, 17a, 17b

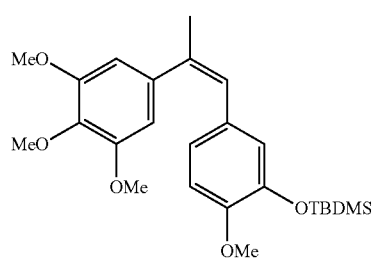

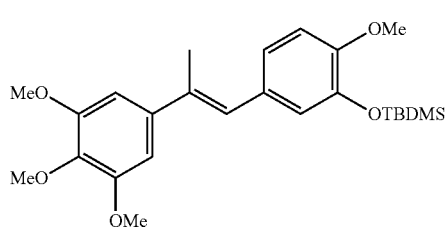

To a slurry of 3-t-butyldimethylsilyloxy-4-methoxybenzylphosphonium bromide, 18, (1 g, 1.69 mmol) in THF (10 ml) was added n-butyllithium (1.16 ml of 1.6 M solution, 1.86 mmol) at −15° C. The red anion was stirred for 20 minutes and 3,4,5-trimethoxyacetophenone (355 mg, 1.69 mmol) added. The resultant solution was stirred at room temperature for 1 hour and water (10 ml) carefully added. The aqueous layer was separated and extracted with ether (3×10 ml). The combined organic layers were washed with water (2×10 ml) and brine (10 ml), dried (MgSO$_4$) and concentrated in vacuo.

Following flash column chromatography (SiO$_2$ petrol:EtOAc 19:1) the Z stilbene, 17a, was isolated as a colourless oil (109 mg, 15%). R$_f$=0.72 (SiO$_2$ petrol:EtOAc 1:1); δ$_H$ (300 MHz) 0.20 [6H, s, (CH$_3$)$_2$], 1.03 [9H, s, (CH$_3$)$_3$], 2.28 (3H, d, J=1.1, CH$_3$), 3.85 (3H, s, OCH$_3$), 3.89 (3H, s, OCH$_3$), 3.93 [6H, s, (OCH$_3$)$_2$], 6.69 (1H, q, J=1.1, olefinic H), 6.72 (2H, s, H-2′,6′) 6.87 (1H, d, J=8.3, H-5″), 6.91 (1H, d, J=2.3, H-2″), 6.95 (1H, dd, J=8.3, 2.3, H-6″); λ$_{max}$ (MeOH)=270 (ε=7,607); M$^+$, found 444.2329; C$_{25}$H$_{36}$O$_5$Si requires M$^+$ 444.2332.

Further elution afforded the E stilbene, 17b, as a colourless oil (258 mg, 34%). R$_f$=0.67 (SiO$_2$ petrol:EtOAc 1:1); δ$_H$ (300 MHz) 0.01 [6H, s, (CH$_3$)$_2$], 0.92 [9H, s, (CH$_3$)$_3$], 2.17 (3H, d, J=1.5, CH$_3$), 3.75 [6H, s, (OCH$_3$)$_2$], 3.76 (3H, s, OCH$_3$), 3.87 (3H, s, OCH$_3$), 6.35 (1H, q, J=1.5, olefinic H), 6.42 (2H, s, H-2′,6′) 6.52 (1H, d, J=1.9, H-2″), 6.62 (1H, dd, J=8.3, 1.9, H-6″), 6.67 (1H, d, J=8.3, H-5″); λ$_{max}$ (MeOH)=296 (ε=16,541). M$^+$, found 444.2333; C$_{25}$H$_{36}$O$_5$Si requires M$^+$ 444.2332.

Z-(3′-Hydroxy-4′-methoxyphenyl)-2-(3″,4″,5″-trimethoxyphenyl)propene, 19

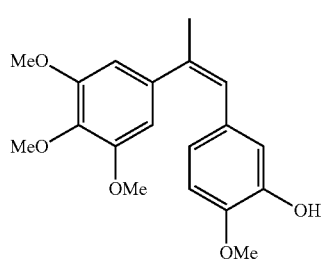

To a stirred solution of Z-(3′-t-butyldimethylsilyloxy-4′-methoxyphenyl)-2-(3″,4″,5″-trimethoxyphenyl)propene, 17a, (111 mg, 0.250 mmol) in dry THF (5 ml) was added tetra-n-butylammonium fluoride (700 ml of 1 M solution, 0.7 mmol). The resulting yellow solution was stirred for 20 minutes and then treated with water (2 ml). The aqueous layer was separated and extracted with chloroform (3×10 ml). The combined organic layers were washed with water (2×10 ml) and brine (10 ml), dried (MgSO$_4$) and concentrated in vacuo. Flash column chromatography (SiO$_2$ petrol:EtOAc 2:1) afforded Z-(3′-hydroxy-4′-methoxyphenyl)-2-(3″,4″,5″-trimethoxyphenyl)propene, 19, as a fine white powder (49 mg, 0.148 mmol, 60%). m.p. 156-8° C.; R$_f$=0.36 (SiO$_2$ petrol: EtOAc 2:1); δ$_H$ (300 MHz) 2.18 (3H, d, J=1.5, CH$_3$), 3.75 [6H, s, (OCH$_3$)$_2$], 3.84 (3H, s, OCH$_3$), 3.88 (3H, s, OCH$_3$), 5.42 (1H, s, OH), 6.36 (1H, q, J=1.5, olefinic H), 6.43 (2H, s, H-2′,6′) 6.48 (1H, dd, J=8.3, 2.3, H-6″), 6.62 (1H, d, J=8.3, H-5″), 6.63 (1H, d, J=2.3, H-2″); λ$_{max}$ (MeOH)=270 (ε=11,524); M$^+$, found 330.1469; C$_{19}$H$_{22}$O$_5$ requires M$^+$ 330.1467.

Z-1-(3′,4′,5′-trimethoxyphenyl)-2-(3″-hydroxy-4″-methoxyphenyl)propene, 20

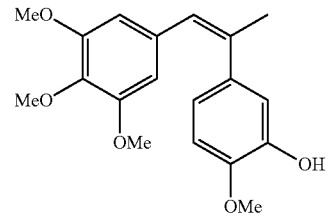

A mixture of cis-1-(3′,4′,5′-trimethoxyphenyl)propene 21 (0.42 g, 2 mmol), 5-iodo-2-methoxyphenol 22 (1 g, 4 mmol), triethylamine (0.51 g, 5 mmol), palladium acetate (9 mg, 0.04 mmol) and triphenylphosphine (21 mg, 0.08 mmol) were heated at 100° C. To the cooled reaction mixture was added aqueous hydrochloric acid (45 ml of a 2.7 M solution). After stirring for 10 min, the liquid was decanted off and the solid residue extracted with several portions of hot hexane. The combined hot hexane fractions were filtered. The cooled hexane solution was washed with water (2×10 ml), brine (10 ml), dried over magnesium sulfate, filtered and the solvent evaporated. Flash column chromatography (SiO$_2$ petrol:EtOAc 15:1) afforded the stilbene (20) as a white crystalline solid (109 mg, 16%). m.p. 99-100° C.; R$_f$=0.34 (SiO$_2$ petrol:EtOAc 1:1); δ$_H$ (300 MHz) 2.28 (3H, d, J=1.1, CH$_3$), 3.89 (3H, s, OCH$_3$), 3.90 (6H, s, 2×OCH$_3$), 3.94 (3H, s, OCH$_3$), 5.61 (1H, s, OH), 6.59 (2H, s, H-2′,6′), 6.74 (1H, q, J=1.1, olefinic H), 6.87 (1H, d, J=8.7, H-5″), 7.04 (1H, dd, J=8.7, 2.3, H-6″), 7.14 (1H, d, J=2.3, H-2″). Found C, 69.13; H, 6.71; C$_{19}$H$_{22}$O$_5$ requires C, 69.07; H, 6.71%; M$^+$, found 331.1541; C$_{19}$H$_{22}$O$_5$ (+H) requires 331.1545; λ$_{max}$ (MeOH)=296 (ε=14,126).

The ethyl derivative (45) has also been synthesised.

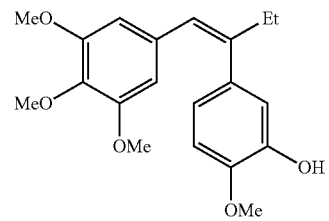 [SMILES: CC/C(=C/c1cc(OC)c(OC)c(OC)c1)c1ccc(OC)c(O)c1]

Z- and E-1-(4′-Methoxyphenyl)-2-(3″,4′,5″-trimethoxyphenyl)propene, 23a, 23b

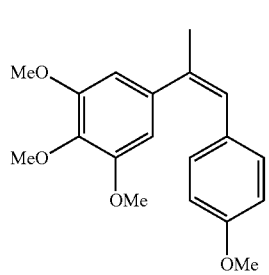

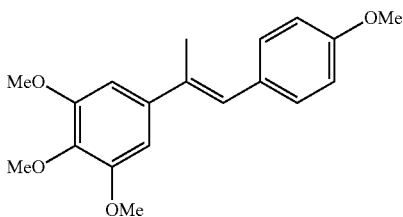

To a slurry of 4-methoxybenzylphosphonium chloride (598 mg, 1.43 mmol) in THF (8 ml) was added n-butyllithium (990 ml of 1.6 M solution, 1.58 mmol) at −15° C. The red anion was stirred for 20 minutes and 3,4,5-trimethoxyacetophenone (300 mg, 1.43 mmol) added. The resultant solution was stirred at room temperature for 1 hour and water (10 ml) carefully added. The aqueous layer was separated and extracted with ether (3×10 ml). The combined organic layers were washed with water (2×10 ml) and brine (10 ml), dried (MgSO$_4$) and concentrated in vacuo.

The nmr of the crude reaction product showed that the Z:E ratio was 1:1.5. Following flash column chromatography (SiO$_2$ petrol:EtOAc 9:1) the Z stilbene, 23a, was isolated as white needles (45 mg, 0.143 mmol, 10%). m.p. 73-5° C.; R$_f$=0.46 (SiO$_2$ petrol:EtOAc 3:1); δ$_H$ (300 MHz) 2.19 (1H, d, J=1.5, CH$_3$), 3.74 [6H, s, (OCH$_3$)$_2$], 3.76 (3H, s, OCH$_3$), 3.88 (3H, s, OCH$_3$), 6.40 (1H, q, J=1.5, olefinic H), 6.42 (2H, s, H-2',6'), 6.69 (1H, dt, J=8.7, 2.3, H-3",5"), 6.93 (1H, dt, J=8.7, 2.3, H-2",6"); λ$_{max}$ (MeOH)=273 (ε=14,926).

Further elution afforded the E stilbene, 23b, as an off white solid (44 mg, 0.140 mmol, 9.8%). m.p. 80-2° C.; R$_f$=0.41 (SiO$_2$ petrol:EtOAc 3:1); δ$_H$ (300 MHz) 2.28 (1H, d, J=1.5, CH$_3$), 3.86 (3H, s, OCH$_3$), 3.90 (3H, s, OCH$_3$), 3.94 [6H, s, (OCH$_3$)$_2$], 6.74 (2H, s, H-2',6'), 6.75 (1H, q, J=1.5, olefinic H), 6.94 (1H, dt, J=8.7, 2.3, H-3",5"), 7.34 (1H, dt, J=8.7, 2.3, H-2",6"); λ$_{max}$ (MeOH)=287 (ε=21,822).

Example 2

Synthesis of Combretastatins with Alkyl Groups Replacing the Methoxy Groups on the A Ring E-2-(3',4',5'-trimethylphenyl)-3-(3"-(2''',3''',5''',6'''-tetrafluoropyridoxy)-4"-methoxyphenyl)prop-2-enoic acid, 24

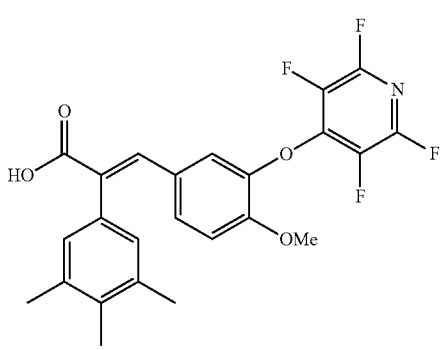

A mixture of 3-(2',3',5',6'-tetrafluoropyridoxy)-4-benzaldehyde 25 (2 g, 6.64 mmol), 3,4,5-trimethylphenylacetic acid 26 (2.37 g, 13.3 mmol) acetic anhydride (6 ml) and triethylamine (3 ml) were heated under reflux for 3 h. After acidification with concentrated hydrochloric acid (9 ml), the solid was filtered off and recrystallised from ethanol to give E-2-(3',4',5-trimethyl)-3-(3"-(2''',3''',5''',6'''-tetrafluoropyridoxy)-4"-methoxyphenyl)prop-2-enoic acid 24 as a yellow crystalline solid (700 mg, 1.52 mmol, 23%). m.p. 184-6° C. δ$_H$ (300 MHz, DMSO) 2.11, (3H, s, CH$_3$), 2.14 (6H, s, (CH$_3$)$_2$), 3.83 (3H, s, OCH$_3$), 6.61 (1H, d, J=1.5, H-2"), 6.71 (2H, s, H-2',6'), 7.13 (1H, d, J=8.7, H-5"), 7.19 (1H, dd, J=8.7, 1.5, H-6"), 7.61, (1H, s, olefinic H), 12.52, (1H, s OH).

(Z)-1-(3',4',5'-trimethylphenyl)-2-(3"-(2''', 3''',5''',6'''-tetrafluoropyridoxy)-4"-methoxyphenyl)ethene, 27

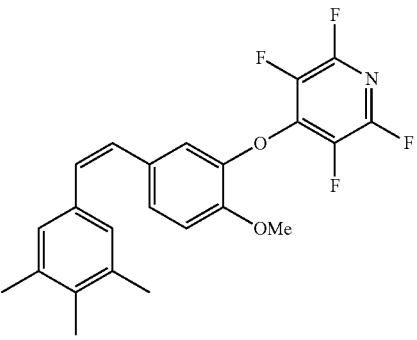

(E)-2-(3',4',5'-trimethylphenyl)-3-(3"-(2''', 3''',5'',6'''-tetrafluoropyridoxy)-4"-methoxyphenyl)prop-2-enoic acid 24 (700 mg, 1.52 mmol) was added to powdered copper (500 mg, 7.81 mmol) in quinoline (5.5 ml, 6.02 g, 28.2 mmol) and the resulting mixture was heated at 200° C. for 2 h. Upon cooling, ether was added and the copper filtered off through celite. The filtrate was washed with 1 M hydrochloric acid (2×20 ml) and the aqueous layer separated and extracted with ether (3×50 ml). The combined organic layers were washed with saturated sodium carbonate (50 ml), water (2×50 ml) and brine (50 ml), dried (MgSO$_4$) and concentrated in vacuo. Flash column chromatography (SiO$_2$ petrol:EtOAc 9:1) afforded (Z)-1-(3',4',5'-trimethylphenyl)-2-(3"-(2''',3''',5''', 6'''-tetrafluoropyridoxy)-4"-methoxyphenyl)ethene 27 as a yellow oil (224 mg, 0.538 mmol, 35%). R$_f$=0.48 (SiO$_2$ petrol:EtOAc 9:1); 86 (300 MHz) 2.15 (3H, s, CH$_3$), 2.19 [6H, s, (CH$_3$)$_2$], 3.84 (3H, s, OCH$_3$), 6.41 (1H, d, J=12.1, olefinic H), 6.51 (1H, d, J=12.1, olefinic H), 6.87 (2H, s, H-2',6'), 6.89 (1H, d, J=8.7, H-5"), 6.98 (1H, d, J=2.3, H-2"), 7.11 (1H, dd, J=8.7, 2.3, H-6").

(Z)-1-(3',4',5'-trimethylphenyl)-2-(3"-hydroxy-4"-methoxyphenyl)ethene, 28

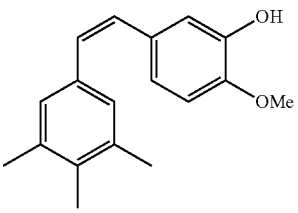

To a solution of the (Z)-1-(3',4',5'-trimethylphenyl)-2-(3"-(2''',3''',5''',6'''-tetrafluoropyridoxy)-4"-methoxyphenyl) ethene (100 mg, 0.24 mmol) 27 in dry DMF (600 ml) and dichloromethane (115 ml) at 0° C. was added sodium methoxide (25 mg, 0.463 mmol). After stirring overnight, the mixture was partitioned between ether (5 ml) and 1 M sulfuric acid (5 ml). The organic phase was washed with water (5 ml), dried (MgSO$_4$) and concentrated in vacuo. Flash column chromatography (SiO$_2$ petrol:EtOAc 9:1) and recrystallisation from petrol afforded (Z)-1-(3',4',5'-trimethylphenyl)-2-(3"-hydroxy-4"-methoxyphenyl)ethene as a white crystalline solid (31 mg, 0.116 mmol, 48%). m.p. 60-1° C. R$_f$=0.39 (SiO$_2$ petrol:EtOAc 4:1); $\delta_H$ (300 MHz) 2.16 (3H, s, CH$_3$), 2.21 [6H, s, (CH$_3$)$_2$], 3.90 (3H, s, OCH$_3$), 5.50 (1H, s, OH), 6.40 (1H, d, J=12.4, olefinic H), 6.45 (1H, d, J=12.4, olefinic H), 6.72 (1H, d, J=8.3, H-5"), 6.82 (1H, dd, J=8.3, 2.3, H-6"), 6.91 (1H, d, J=2.3, H-2"), 6.96 (2H, s, H-2',6').

Example 3

Synthesis of Combretastatins with a 3,4,5 Trialkoxy Group

Z- and E-1-(3',4',5'-triethoxyphenyl)-2-(3"-t-butyldimethylsilyloxy-4"-methoxyphenyl)ethene, 30a, 30b To a slurry of 3,4,5-triethoxybenzylphosphonium bromide 29 (2 g, 3.24 mmol) in THF (30 ml) was added n-butyllithium (2.5 ml of 1.6M solution in hexanes, 4 mmol) at −15° C. under argon. The red anion was stirred for 20 min and 3-O-t butyldimethylsilyl-4-methoxybenzaldehyde 6 (0.86 g, 3.24 mmol) added. The resultant solution was stirred for 1 h at room temperature and water (10 ml) was carefully added. The aqueous layer was separated and extracted with ethyl acetate (3×100 ml). The combined organic layers were washed with water (2×100 ml), brine (100 ml), dried (MgSO$_4$) and concentrated in vacuo. Flash column chromatography afforded the cis stilbene 30a as a colourless oil (0.23 g, 15%). R$_f$=0.65 (petrol:ethyl acetate 9:1); $\delta_H$ (300 MHz) 0.08 (6H, s, Si(C$\underline{H}_1$)$_2$), 0.95 (9H, s, 3×CH$_3$), 1.35 (9H, m, 3×OCH$_2$C$\underline{H}_3$), 3.79 (3H, s, OCH$_3$), 3.91 (4H, q, J=6.8, CH$_2$), 4.06 (2H, q, J=7.2, CH$_2$), 6.40 (1H, d, J=12.1, olefinic H), 6.43 (1H, d, J=12.1, olefinic H), 6.74 (2H, s, ArH 2, 6), 6.83 (1H, dd, J=8.0, 2.1, ArH para to OSi), 6.84 (1H, d, J=8.0, ArH ortho to OMe), 6.88 (1H, d, J=2.1, ArH ortho to OSi).

Further elution gave the trans stilbene 30b as white crystals (0.27 g, 17.6%). R$_f$=0.75; $\delta_H$ (300 MHz) 0.20 (6H, s, Si(C$\underline{H}_3$)$_2$), 1.03 (9H, s, 3×CH$_3$), 1.37 (3H, t, J=7.5, CH$_2$C$\underline{H}_3$), 1.46 (6H, t, J=7.2, 2×CH$_2$C$\underline{H}_3$), 3.85 (3H, s, OCH$_3$), 4.12 (6H, m, 3×CH$_2$), 6.73 (2H, s, ArH 2, 6), 6.84 (1H, dd, J=7.8, 1.98, ArH para to OSi), 6.90 (1H, d, J=15.1, olefinic H), 7.04 (1H, d, J=7.8, ArH ortho to OMe), 7.05 (1H, d, J=15.1, olefinic H), 7.66 (1H, d, J=2.0, ArH ortho to OSi).

Z- and E-1-(3',4',5'-triethoxyphenyl)-2-(3"-hydroxy-4"-methoxyphenyl)ethene, 31a, 31b To a stirred mixture of cis and trans-1-(3',4',5'-triethoxyphenyl)-2-(3"-tert-butyldimethylsiloxy-4"-methoxy)ethene 30a, 30b (0.23 g, 0.48 mmol-cis isomer; 0.27 g, 0.57 mmol-trans isomer) in dry THF (17.5 ml) was added tetra-n-butylammonium fluoride (1.46 ml of 1 M solution in THF). The resulting yellow solution was stirred for twenty min and treated with water (50 ml). The aqueous layer was separated and extracted with chloroform (3×50 ml). The combined organic layers were washed with water (2×50 ml) and brine (50 ml), dried (MgSO$_4$) and concentrated in vacuo.

Flash column chromatography (petrol:ethyl acetate 4:1) afforded Z-1-(3',4',5'-triethoxyphenyl)-2-(3"-hydroxy-4"-methoxyphenyl)ethene 31a as a colourless oil (0.08 g, 46%). R$_f$=0.24. $\delta_H$ (300 MHz) 1.34 (9H, m, 3×CH$_2$C$\underline{H}_3$), 3.87 (3H, s, OCH$_3$), 3.92 (4H, q, J=7.2, 2×CH$_2$), 4.06 (2H, q, J=7.2, CH$_2$), 6.40 (1H, d, J=12.43, olefinic H), 6.45 (1H, d, J=12.4, olefinic H), 6.50 (2H, s, ArH 2,6), 6.75 (1H, d, J=8.1, ArH ortho to OMe), 6.79 (1H, dd, J=8.7, 1.88, ArH para to OH), 6.91 (1H, d, J=1.9, ArH ortho to OH). M$^+$, 358.

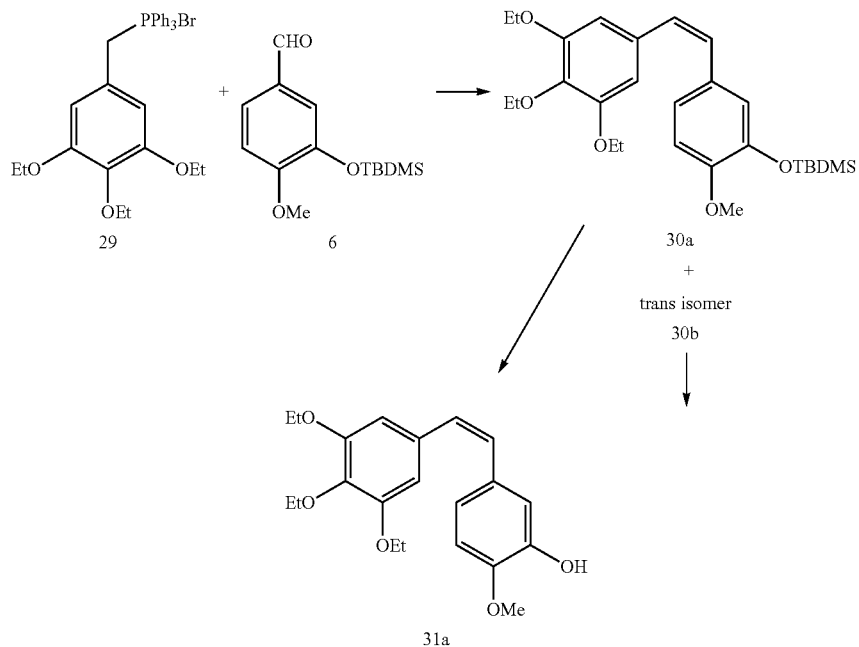

Further elution afforded E-1-(3',4',5'-triethoxyphenyl)-2-(3"-hydroxy-4"-methoxyphenyl)ethene 31b (0.09 g, 46.6%) as white crystals. mp: 91-92° C.; R$_f$=0.11. $\delta_H$ (300 MHz) 1.37

(3H, t, J=6.0, CH$_3$), 1.46 (6H, t, J=6.4, 2×CH$_3$), 3.92 (3H, s, OCH$_3$), 4.12 (6H, m, 3×CH$_2$), 6.71 (2H, s, H 2, 6), 6.84 (1H, d, J=7.8, ArH ortho to OMe), 6.85 (1H, d, J=15.5, olefinic H), 6.91 (1H, dd, J=7.9, 2.26, ArH para to OH), 7.11 (1H, d, J=15.5, olefinic H), 7.13 (1H, d, J=2.3, ArH ortho to OH). M$^+$, 358.

Z- and E-1-(3',4',5'-triethoxyphenyl)-2-(3''-fluoro-4''-methoxyphenyl)ethene, 32a, 32b To a slurry of 3,4,5-triethoxybenzylphosphonium bromide 29 (2 g, 3.24 mmol) in THF (30 ml) was added n-butyllithium (2.5 ml of 1.6 M solution in hexanes, 4 mmol) at −15° C. under argon. The red anion was stirred for 20 min and 3-fluoro-4-methoxybenzaldehyde (0.50 g, 3.24 mmol) was added. The resultant solution was stirred for 1 h and water (10 ml) was carefully added. The aqueous layer was separated and extracted with ethyl acetate (3×100 ml). The combined organic layers were washed with water (2×100 ml) and brine (100 ml), dried (MgSO$_4$) and concentrated in vacuo.

Flash column chromatography (SiO$_2$, petrol:ethyl acetate 20:1) afforded the cis-stilbene 32a as a pale yellow oil (0.35 g, 29%), R$_f$=0.16; δ$_H$ (300 MHz) 1.35 (9H, m, 3×CH$_3$), 3.87 (3H, s, OCH$_3$), 3.92 (4H, q, J=6.8, 2×CH$_2$), 4.07 (2H, q, J=7.2, CH$_2$), 6.41 (1H, d, J=12.4, olefinic H), 6.47 (1H, d, J=12.4, olefinic H), 6.47 (2H, s, ArH 2,6), 6.84 (1H, t, J=8.7, ArH ortho to OMe), 7.00 (1H, dd, J=8.7, 1.5, ArH para to F), 7.05 (1H, d, J=12.1, 1.5, ArH ortho to F). M$^+$, 360.

Further elution afforded the trans isomer 32b (0.27 g, 23%) as white needles mp:97-99° C.; Rf=0.22; δ$_H$ (300 MHz) 1.38 (6H, t, J=7.2, 2×CH$_3$), 1.46 (3H, t, J=7.2, CH$_3$) 3.92 (3H, s, OCH$_3$), 4.12 (6H, m, 3×CH$_2$), 6.71 (2H, s, H 2,6) 6.91 (1H, d, J=15.5, olefinic H), 6.94 (1H, t, J=8.7, ArH ortho to OMe), 6.95 (1H, d, J=15.5, olefinic H), 7.17 (1H, dd, J=8.7, 2.3 ArH para to F), 7.25 (1H, dd, J=12.0, 2.3, ArH ortho to F). M$^+$, 360.

Example 4

Boc-Combretastatin Compounds

Boc-Phenylalanine Combretastatin A-4, 33

To a stirred solution of t-butoxycarbonyl-phenylalanine (168 mg, 0.634 mmol), dicyclohexylcarbodiimide (157 mg, 0.76 mmol), N,N-4-dimethylaminopyridine (8 mg, 61 µmol) in dichloromethane (15 ml) under nitrogen at room temperature in the dark was added combretastatin A-4 (1) (200 mg, 0.633 mmol). After stirring for 48 h, the mixture was filtered, evaporated and the residue chromatographed on silica using petroleum (bp 40-60° C.)/ethyl acetate 4:1 to afford the title ester (33) as a clear gum (143 mg, 40%). ν$_{max}$ 3364 (NH); 1766, 1716 (C=O). 6, 7.22 (5H, m, phenylalanine ArHs); 7.11 (1H, dd, J=8.1, 2.0, H para to O ester); 6.95 (1H, d, J=2.0, H ortho to O ester); 6.83 (1H, d, J=2.0, H meta to O ester); 6.40, 6.50 (4H, 2 s, olefinic Hs, A-ring Hs); 5.07 (1H, broad, NH); 4.80 (1H, m, H-α); 3.80, 3.70, 3.66 (12H, 3×s, 4×OMe); 3.35-3.08 (2H, m, CH$_2$); 1.40 (9H, s, 3×CH$_3$). λ$_{max}$ 241; 271; 305. m/z 463 (35%, M+H—BOC); 317 (100).

The other BOC compounds 34-44 were made using the above method.

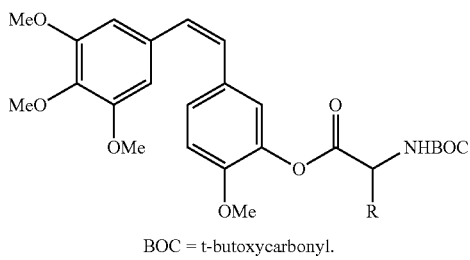

BOC = t-butoxycarbonyl.

| 33 | R = Phe | 39 | R = Ala |
| --- | --- | --- | --- |
| 34 | R = Ile | 40 | R = His |
| 35 | R = Gly | 41 | R = Pro |
| 36 | R = Trp | 42 | R = D-Met |
| 37 | R = Met | 43 | R = D-Trp |
| 38 | R = Leu | 44 | R = Tyr |

Example 5

Benzoquinone Compounds

2-Methoxy-5-[(Z)-2-(3',4',5'-trimethoxyphenyl)-vinyl]-[1,4]benzoquinone 97-96

To a mixture of Aliquat 336 (0.181 ml, 1.25 equiv) and NaH$_2$PO$_4$.H$_2$O (323 mg, 2.34 mmol) in water (100 ml) was added a solution of combretastatin A4 (1) (100 mg, 0.316 mmol) in dichloromethane (7 ml). Fremy's salt (potassium nitrosodisulfonate) (212 mg, 0.8 mmol) was added and the mixture shaken for 30 min. (Colour changes from mauve to red). The dichloromethane was collected and the aqueous fraction extracted with dichloromethane (3×10 ml). The combined organic phases were washed with water (3×10 ml), brine (10 ml) and dried over magnesium sulfate. Evaporation of the solvent followed by flash chromatography of the residue using petrol:ethyl acetate (65:35) as eluent afforded the quinone as a red crystalline solid (51 mg, 49%) mp 130-2° C., δ$_H$ (acetone d6) 3.70, 3.75, 3.85 (12H, 3 s, 4×OMe); 6.08 (1H, s, quinone-H ortho to OMe); 6.43 (1H, dd, J 12.5, 0.5, olefinic-H next to quinone ring); 6.67 (1H, d, J 0.5, quinone-H meta to OMe); 6.73 (2H, s, ArHs); 6.96 (1H, d, J, 12.5, olefinic-H next to Ar ring). λ$_{max}$ 296 (ε12,708); 470 (2038). ν$_{max}$ 1666, 1647 cm$^{-1}$. M+, 330 (40%); 315 (M-Me, 60); 69 (100).

This method was also used to synthesise 98-40, 98-23, 98-33 and 98-24.

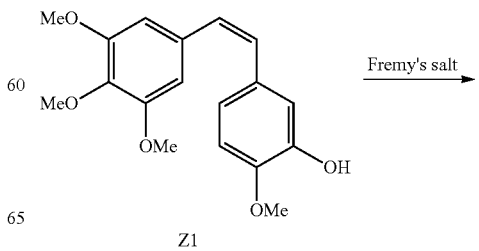

-continued

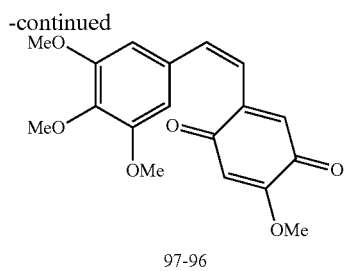

97-96

These quinones may act as prodrugs producing the active hydroquinones on reduction by enzymes.

Example 6

Biological Activity of Compounds

The following assays (1-5) were carried out as described in our paper (Woods, et al, British Journal of Cancer, 71, 705-711 (1995)). In addition to the cell lines described in this paper, other established human cell lines (K562, HUVEC, H460, BE, H529, and HT29) were used in the cytotoxicity/growth inhibition assay.

(1) Inhibition of tubulin assembly. The figure quoted is the concentration required to reduce assembly of tubulin by 50%. Tubulin assembly is monitored by light scatter/absorption at 350 nm.

(2) Competition for the colchicine binding site on tubulin. The figure quoted represents the % of $^3$H-colchicine bound following co-incubation of test compound and $^3$H-colchicine with isolated tubulin. Where ester pro-drugs were used the experiments were carried out in the presence and absence of porcine liver esterase.

(3) Cytotoxicity/growth inhibition assay. This was carried out by the MTT assay.

(4) Permeability (shape-change) assay in endothelial cells. This was carried out using a method based on that of Watts et al. (Anticancer Res., 17, 71-75, (1997)). This involved the diffusion of a fluorescently labelled dextran through a barrier of endothelial cells (HUVEC) grown to confluence on a porous membrane. The effect of agents to alter the shape of these cells results in an increase in the permeability of the cells to the dye. The figure represents the increase in permeability over control cultures when drug is added (30 minutes, 1 mM.).

(5) Experiments to study the anti-vascular effects of these agents were carried out as described previously by our group. (Zhao et al, European Journal of Nuclear Medicine, 26, 231-238 (1999)). The anti-vascular effects of the agents were monitored by either positron emission tomography (PET) or by histological examination following treatment of mice bearing T50:80 murine breast tumours, or H460 human lung tumours.

(6) Anti-tumour efficacy of agents was determined in xenografts of H460 human lung cancer. Animals (n=5) were treated either with 5 daily injections and tumour size measured with time following treatment.

(7) The pharmacokinetic profile of agents was determined in mice following injection with drug. Blood was taken at various times following treatment and analysed by HPLC with UV detection. The HPLC conditions were isocratic using a 5 micron C18 BDS column (150×4.6) and eluting with 75% MeOH in water with a detection wavelength of 290 nm. The retention time of 6.6 mins for 97-64H.

(8) Activation of quinone prodrugs by DT-diaphorase. (NAD(P)H:quinone oxidoreductase, EC 1.6.99.2). DT-diaphorase is an enzyme over-expressed in a number of human tumours. We have recently shown this enzyme to be highly expressed in the endothelial cells of blood vessels. This two-electron reducing enzyme can be used to selectively activate prodrugs within cancers which over-express the enzyme. We have therefore synthesised quinone pro-drugs (97-96, 98-40, 98-23, 98-33, 98-24) which, upon reduction by the enzyme, produces an agent (a hydroquinone stilbene) which is cytotoxic.

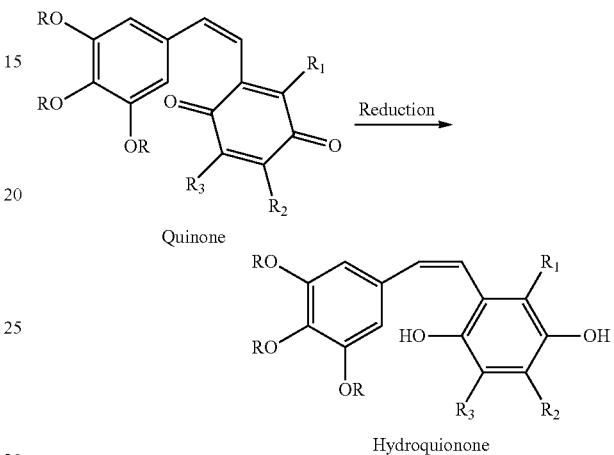

Results

The in vitro studies reported in Table 11 illustrate the structural requirements necessary for biological activity. Modifications of the A ring have shown that the methoxy groups can be replaced by alkoxy or alkyl (28,31a,32a) whilst retaining their ability to inhibit assembly of isolated tubulin. Similarly, molecules with alkyl substituents on the ethene bridge (19,20,46) retain activity both as inhibitors of tubulin assembly and are growth inhibitory in vitro. The pharmacophore consists of a stilbene in a cis configuration with a small alkyl or O-alkyl substituent at the 4-position of the B ring. Substitution at the 3-position of the B-ring with F results in highly active compounds that are potent inhibitors of tubulin assembly, and are potently growth inhibitory (97-64H, and 98-35). These agents show good activity in the shape-change (permeability) assay. This test is used as an in vitro assay of vascular damage. 97-64H also shows anti-tumour activity in vivo in H460 human lung cancer xenografts. 97-64H was given at either ⅔ of the maximum tolerated dose (MTD=200 mg/kg) or at % of the MTD to mice bearing liver metastatic T50:80 tumours. Tumours were removed and examined for evidence of vascular damage at 2 hr and 4 hr following drug administration. Similarly a dose equivalent to of the MTD was administered and the tumours examined 24 hr and 48 hr following administration of drug. Examination of these tumours showed tumour necrosis, blocked vessels, infiltration with red blood cells, consistent with damage to the vasculature. These effects are seen within 2 hours. 97-64H is orally bio-available when administered at 200 mg/kg in 5% dimethylacetamide in arachis oil, 97-64H showed a Cmax of 1.49 ug/ml, an absorption half life 15 mins, and an elimination half life 32 mins. The concentration achieved in vivo (1.49 mg/ml=4.6 mM) is far in excess of the concentration necessary to inhibit the growth of HUVEC cells in vitro (0.001 mM) indicating that this agent is bio-available when administered orally.

The 3-position of the B-ring can also be substituted with larger groups such as boc-amino acid esters, pyridyl esters, and ethers. The amino acid esters (33-44) are prodrugs which, upon the action of esterase, release the active agent. The activity of these agents is related to the rate of hydrolysis of these agents by esterase. The most active compounds being those which are most readily hydrolysed. The activity of these compounds indicates that ester linked polymers and peptides would be good prodrugs for agents of this type (see Table 1).

The pyridyl esters (96-167 and 97-07) are potent inhibitors of tubulin assembly and can displace $^3$H-colchicine from tubulin without the action of esterase, showing that the 3-position of the B-ring can be substituted with bulky side groups. Potent growth inhibitory activity and good activity in the shape-change assay can also be seen for the tetrafluoropyridyl ether (97-13) and other ethers (98-29) which are not a substrate for esterase.

A series of prodrugs capable of being activated by DT-diaphorase, an enzyme over-expressed in a wide range of human cancers and in endothelial cells of the vasculature were synthesised. The rationale for this is that these agents will be activated in situ by the tumours over-expressing the enzyme, thus giving rise to a high local concentration of active drug. This confers selectivity to this agent. These quinone prodrugs (97-96 and 98-23) were tested for their ability to act as substrates for DT-diaphorase. It can be seen that these compounds are good substrates for the enzyme, and are comparable to RH1 (2,5,-diaziridinyl-3-(hydroxymethyl)-6-methyl-1,4-benzoquinone) a novel alkylating agent which is activated by DT-diaphorase and is currently about to enter clinical trial. An analysis of the growth inhibitory properties of these agents shows that 97-96 is 16-fold more active in the H460 human lung cell line which expresses active DT-diaphorase than in the diaphorase null H596 cell line 97-96 is active in an H460 human lung tumour xenograft, a tumour which expresses active DT-diaphorase. This agent may therefore have a role in the treatment of tumours that over-express DT-diaphorase. Similarly, these agents maybe selectively activated in the endothelial cells of the vasculature, thereby conferring a selective anti-vascular effect.

TABLE 1

| Compound | IC$_{50}$ (nM) A2780 | IC$_{50}$ (nM) A2780/ADR | Inhibition of tubulin assembly (IC$_{50}$ μM) | Colchicine displacement protein:drug 1:10 (with esterase) | Colchicine displacement protein:drug 1:10 (without esterase) |
|---|---|---|---|---|---|
| 1 | 0.72 | 0.84 | 2.4 | NA | 12 |
| 33 | 2.8 | 4.0 | 3.6* | 2 | 92 |
| 34 | >60 | >60 | 6.2* | 2 | 65 |
| 35 | 4.3 | 5.0 | 7.5* | 4 | 65 |
| 36 | 1.7 | 2.0 | 4.0* | ND | ND |
| 37 | 6.7 | 9.1 | 6.0* | 2 | 88 |
| 38 | 14.0 | 27.0 | 7.8* | ND | 72 |
| 39 | 2.7 | 4.6 | 8.0 | 2 | 77 |
| 40 | 2.2 | 4.3 | 7.0* | 4 | 2 |
| 41 | 29.0 | 39.0 | 9.0* | 2 | 78 |
| 42 | 2.9 | 2.9 | 3.5* | 2 | ND |
| 43 | 3.3 | 3.8 | 3.0* | 2 | ND |
| 44 | 4.5 | 6.4 | ND | ND | ND |

TABLE 2

| Compound | P388 | A2780 | H460 | H596 | H596/H460 |
|---|---|---|---|---|---|
| A-4 | 2.6 | 0.72 | 1.51 | | |
| 97-96 | 570 | 190 | 38 | 620 | 16 |
| 98-40 | >5000 | 4630 | >5000 | 2190 | <0.44 |
| 98-23 | 2180 | 2150 | 4370 | 2280 | 0.52 |
| 98-33 | <780 | 950 | 4110 | 1490 | 0.36 |
| 98-24 | 17050 | 1630 | 3080 | 1950 | 0.63 |

IC$_{50}$ are in nM.

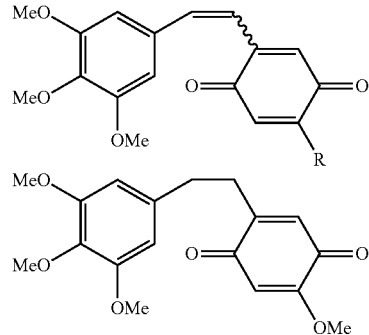

97-96 R=OMe (cis) 98-24
98-40 R=OMe (trans)
98-23 R=Me (cis)
98-33 R=Me (trans)

Example 7

Synthesis of Combrestatatin A-4 Bearing a Photocleavable Group Methyl 4-(4'-formyl-2'-methoxyphenoxy)butanoate 4

(see D. L. McMinn and M. M. Greenberg, Tetrahedron, 1996, 52, 3827)

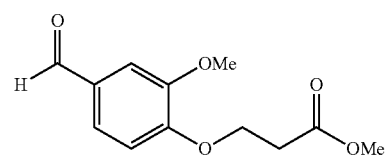

To a stirred solution of vanillin (3)(2 g, 13.16 mmol) and methyl 4-bromobutyrate (2.38 g, 13.16 mmol) in DMF (20 cm$^3$) was added freshly ground anhydrous potassium carbonate (2.03 g, 14.47 mmol). The resulting pale pink suspension was heated at 100° C. for 90 mins, after which time the suspension has become milky pink in appearance. The mixture was then poured into water (50 cm$^3$) and extracted with Et$_2$O (3×30 cm$^3$). The combined organic extracts were washed with water (2×30 cm$^3$), then 1M HCl (2×30 cm$^3$) before being dried (MgSO$_4$) and concentrated in vacuo. The pale pink solid 4 was used without further purification (2.7 g, 82%). m.p. 69° C. [lit. (D. L. McMinn and M. M. Greenberg, Tetrahedron, 1996, 52, 3827) m.p. 68-69° C.]. Found C, 62.0; H, 6.3; C$_{13}$H$_{16}$O$_5$ requires C, 62.0; H, 6.4%; R$_f$ 0.44 (SiO$_2$, hexane:EtOAc, 2:1 v/v); ν$_{max}$ (KBr disc)/cm$^{-1}$ 3100-2700 (m), 1740 (s), 1680 (s); δ$_H$ (300 MHz, CDCl$_3$) 2.19 (2H, q, J=6.6 Hz, CH$_2$), 2.56 (2H, t, J=6.6 Hz, CH$_2$), 3.68 (3H, s, OCH$_3$), 3.91 (3H, s, OCH$_3$), 4.15 (2H, t, J=6.6 Hz, CH$_2$), 6.97 (1H, d, J=8.0 Hz, H-6'), 7.40 (1H, dd, J=8.0 Hz, J=1.8 Hz, H-5'), 7.44 (1H, d, J=1.8 Hz, H-3'), 9.84 (1H, s, CHO) ppm;

$\delta_C$ (100 MHz, CDCl$_3$) 24.1 (CH), 30.2 (CH$_2$), 51.5 (OCH$_3$), 55.8 (OCH$_3$), 67.3 (CH), 109.2 (CH), 111.5 (CH), 126.6 (CH), 130.0, 149.7, 153.7, 173.3 (COOCH$_3$), 190.8 (CHO) ppm; m/z (FAB) 253 [(MH$^+$), 50%].

Methyl 4-(4'-formyl-2'-methoxy-5'-nitrophenoxy)butanoate 5

(see D. L. McMinn and M. M. Greenberg, *Tetrahedron*, 1996, 52, 3827.)

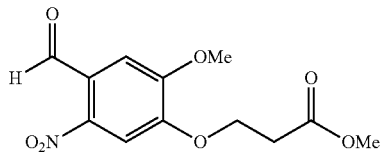

5

To a pale pink solution of methyl 4-(4'-formyl-2'-methoxyphenoxy)butanoate (4) (3 g, 12.3 mmol) in DCM (20 cm$^3$) was added dropwise, at 0° C. fuming nitric acid (1.5 cm$^3$, 37.0 mmol). The resulting green solution was stirred at 00° C. for a further 30 mins before being allowed to spontaneously warm to r.t., where it remained for 3 hours. The subsequent bright yellow suspension was poured onto iced water (50 cm$^3$) and extracted with DCM (3×30 cm$^3$). The combined organic phase was washed with sat. NaHCO$_3$ solution (2×50 cm$^3$), followed by water (2×50 cm$^3$) before being dried and concentrated in vacuo providing a bright yellow solid. The desired compound 5 was used without further purification (2.48 g, 68%). A small amount of material (250 mg, 0.84 mmol) was purified via column chromatography (SiO$_2$, CH$_2$Cl$_2$) so that complete characterisation data could be obtained, m.p. 75° C. [lit. (D. L. McMinn and M. M. Greenberg, *Tetrahedron*, 1996, 52, 3827.) m.p. 76-78° C.]. Found C, 52.7; H, 5.2; N, 4.8; C$_{13}$H$_{15}$NO$_7$ requires C, 52.5; H, 5.1; N, 4.7%; R$_f$ 0.44 (SiO$_2$, CH$_2$Cl$_2$); $\nu_{max}$ (KBr disc)/cm$^{-1}$ 3100-2700 (m), 1735 (s), 1690 (s), 1290, 1220; 6, (200 MHz, CDCl$_3$) 2.23 (2H, q, J=7.1 Hz, CH$_2$), 2.57 (2H, t, J=7.1 Hz, CH$_2$), 3.71 (3H, s, OCH$_3$), 3.99 (3H, s, OCH$_3$), 4.21 (2H, t, J=7.1 Hz, CH$_2$), 7.40 (1H, s, H-3'), 7.61 (1H, s, H-6'), 10.44 (1H, s, CHO) ppm; $\delta_C$ (100 MHz, CDCl$_3$) 24.1 (CH$_2$), 30.2 (CH$_2$), 51.8 (OCH$_3$), 56.6 (OCH$_3$), 59.6 (CH$_2$), 108.1 (CH), 109.9 (CH), 125.5, 143.8, 151.7, 153.4, 173.2 (COOCH$_3$), 187.8 (CHO) ppm; m/z (FAB) 298 [(MH$^+$), 40%].

Methyl 4-[4'-(hydroxymethyl)-2'-methoxy-5'-nitrophenoxy]butanoate 6

(see D. L. McMinn and M. M. Greenberg, *Tetrahedron*, 1996, 52, 3827.)

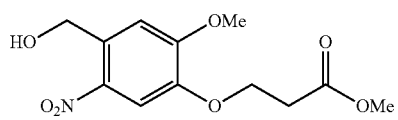

6

To a clear yellow solution of methyl 4-(4'-formyl-2'-methoxy-5'-nitrophenoxy) butanoate (5) (1 g, 3.36 mmol) in THF (10 cm$^3$) was added, portion wise, sodium borohydride (128 mg, 3.36 mmol). The solution quickly changed appearance, becoming deep orange after about 5 mins. The mixture was stirred for a further 55 mins before water was added (25 cm$^3$), the subsequent yellow mixture was extracted with ether (3×30 cm$^3$) and the combined organic extracts were dried (MgSO$_4$) and concentrated in vacuo providing a pale yellow solid. The solid, 6 was used without further purification (875 mg, 87.5%). A small amount of material (200 mg, 0.67 mmol) was purified via column chromatography (SiO$_2$, hexane:EtOAc 2:1 v/v) so that complete characterisation data could be obtained. m.p. 100° C. [lit. (D. L. McMinn and M. M. Greenberg, *Tetrahedron*, 1996, 52, 3827.) m.p. 98-100° C.]. Found C, 52.2; H, 5.7; N, 4.7; C$_{13}$H$_{17}$NO$_7$ requires C, 52.2; H, 5.7; N, 4.7%; R$_f$ 0.24 (SiO$_2$, hexane:EtOAc 2:1 v/v); $\nu_{max}$ (KBr disc)/cm$^{-1}$ 3400-3100 (br), 3000-2800 (m), 1730 (s), 1280, 1220; $\delta_H$ (200 MHz, CDCl$_3$) 2.20 (2H, q, J=7.3 Hz, CH$_2$), 2.56 (2H, t, J 7.3 Hz, CH$_2$), 2.61 (1H, br, OH), 3.70 (3H, s, OCH$_3$), 3.98 (3H, s, OCH$_3$), 4.13 (2H, t, J=7.3 Hz, CH$_2$), 4.95 (2H, s, CH$_2$), 7.15 (1H, s, H-3'), 7.71 (1H, s, H-6') ppm; $\delta_C$ (100 MHz, CDCl$_3$) 24.3 (CH$_2$), 30.4 (CH$_2$), 51.7 (OCH$_3$), 56.4 (OCH$_3$), 62.8 (CH$_2$), 68.3 (CH$_2$), 109.5 (CH), 111.2 (CH), 132.4, 139.6, 147.2, 154.3, 173.4 (COOCH$_3$) ppm; m/z (FAB) 299 [(M$^+$), 15%], 282 [(M-OH), 40%].

Methyl 4-[4'-(bromomethyl)-2'-methoxy-5'-nitrophenoxy]butanoate 7

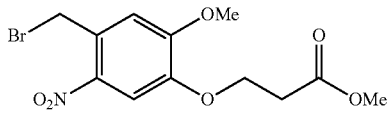

7

To a solution of methyl 4-[4'-(hydroxymethyl)-2'-methoxy-5'-nitrophenoxy]butanoate (6) (750 mg, 2.52 mmol) in anhydrous THF (10 cm$^3$) was added PBr$_3$ (0.24 cm$^3$, 2.52 mmol). The resulting deep yellow solution was refluxed for 3 hours, after which time no visible changes had occurred. The reaction mixture was cooled then poured onto ice. The resulting aqueous solution was extracted with ether (3×30 cm$^3$). The combined organic extracts were washed with 5% NaHCO$_3$ solution (2×30 cm$^3$) and water (2×30 cm$^3$) before being dried (MgSO$_4$) and concentrated in vacuo. The desired compound 7 was furnished as a yellow oil. The oil was then purified via column chromatography (SiO$_2$, hexane:EtOAc, 2:1 v/v) thus providing 7 as a yellow powder (580 mg, 64%). m.p. 68-70° C. Found C, 43.2; H, 4.5; N, 4.0; Br, 21.9; C$_{13}$H$_{16}$NO$_6$Br requires C, 43.1; H, 4.4; N, 3.9; Br, 22.1%; R$_f$ 0.63 (SiO$_2$, hexane:EtOAc 2:1 v/v); $\nu_{max}$ (KBr disc)/cm$^{-1}$ 3000-2800 (m), 1720 (s), 1610, 1580, 1530, 1280, 1220; $\delta_H$ (200 MHz, CDCl$_3$) 2.20 (2H, q, J=6.7 Hz, CH$_2$), 2.56 (2H, t, J=6.7 Hz, CH$_2$), 3.70 (3H, s, OCH$_3$), 3.97 (3H, s, OCH$_3$), 4.13 (2H, t, J=6.7 Hz, CH$_2$), 4.86 (2H, s, CH$_2$), 6.92 (1H, s, H-3'), 7.67 (1H, s, H-6') ppm; $\delta_C$ (100 MHz, CDCl$_3$) 24.1 (CH$_2$), 30.1 (CH$_2$), 51.6 (OCH$_3$), 56.4 (OCH$_3$), 68.0 (CH$_2$), 68.3 (CH$_2$), 109.7 (CH), 113.8 (CH), 127.3, 140.0, 148.1, 153.5, 173.2 (COOCH$_3$) ppm; m/z (FAB) 362 [(MH$^+$), 100%].

Methyl 4-[2'-methoxy-5'-nitro-4'-(phenoxymethyl)phenoxy]butanoate 9

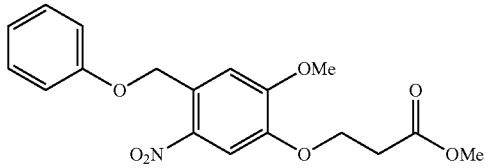

To a suspension of phenol (130 mg, 138 mmol) and methyl 4-[4'-(bromomethyl)-2'-methoxy-5'-nitrophenoxy]butanoate (7) (500 mg, 138 mmol) in anhydrous methanol (5 cm³) was added K'OBu (186 mg, 166 mmol). The resulting green mixture was stirred at r.t. for 30 mins after which time a white precipitate had formed. The precipitate was filtered and recrystallised from methanol affording the desired compound 9 as a pure white solid (319 mg, 61%). m.p. 96-98° C. Found C, 61.0; H, 5.8; N, 4.0; $C_{19}H_{21}NO_7$ requires C, 60.8; H, 5.6; N, 3.7%; $R_f$ 0.64 ($SiO_2$, hexane:EtOAc 2:1 v/v); $\nu_{max}$ (KBr disc)/cm$^{-1}$ 3000-2800 (m), 1720 (s), 1610, 1580, 1520, 1280, 1220; $\delta_H$ (300 MHz, CDCl$_3$) 2.21 (2H, q, J=6.7 Hz, CH$_2$), 2.57 (2H, t, J=6.7 Hz, CH$_2$), 3.71 (3H, s, OCH$_3$), 3.91 (3H, s, OCH$_3$), 4.14 (2H, t, J=6.7 Hz, CH$_2$), 5.50 (2H, s, CH$_2$), 6.98-7.02 (3H, m, ar), 7.29-7.34 (3H, m, ar), 7.77 (1H, s, ar) ppm; $\delta_C$ (100 MHz, CDCl$_3$) 24.7 (CH$_2$), 30.4 (CH$_2$), 51.7 (OCH$_3$), 56.3 (OCH$_3$), 67.0 (CH$_2$), 68.2 (CH$_2$), 109.4 (CH), 109.6 (CH), 115.0 (CH), 121.5 (CH), 129.6 (CH), 129.7 (CH), 138.9, 147.0, 154.3, 158.1, 173.2 (COOCH$_3$) ppm; m/z (FAB) 376 [(MH), 20%], 282 [(M-C$_6$H$_5$O), 80%].

Methyl 4-[2'-methoxy-4'-({2''-methoxy-5''-[(Z)-2'''-3''',4''',5'''-trimethoxyphenyl)ethenyl]phenoxy}-methyl)-5'-nitrophenoxy]butanoate Z-8

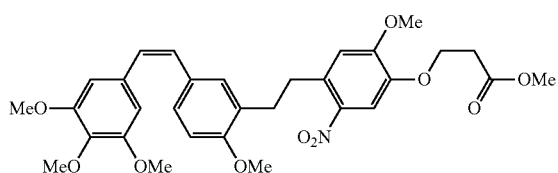

To a suspension of methyl 4-[4'-(bromomethyl)-2'-methoxy-5'-nitrophenoxy]butanoate (7) (1.5 g, 4.14 mmol) and cis-CA-4 (1.6 g, 5.0 mmol) in anhydrous methanol (20 cm³) was added K'OBu (0.58 g, 5.2 mmol). The resulting yellow mixture was stirred at r.t. for 30 mins after which time a yellow precipitate had formed. The precipitate was filtered and recrystallised from methanol furnishing the desired compound Z-8 as a pale yellow solid (1.62 g, 69%). m.p. 132-134° C. Found C, 65.2; H, 6.5; N, 2.4; $C_{31}H_{35}NO_{11}$ requires C, 65.6; H, 6.2; N, 2.5%; Accurate mass; found M$^+$597.2201; $C_{31}H_{35}NO_{11}$ requires M$^+$597.2210; $R_f$ 0.60 (SiO$_2$, hexane:EtOAc 2:1 v/v); $\nu_{max}$ (KBr disc)/cm$^{-1}$ 3000-2800 (m), 1730 (s), 1610, 1580, 1520, 1320, 1280, 1220, 1130, 880; $\lambda_{max}$ (MeCN)/nm 222 ($\epsilon$35050), 242 ($\epsilon$29263) and 293 ($\epsilon$14071); $\delta_H$ (300 MHz, CDCl$_3$) 2.21 (2H, q, J=6.7 Hz, CH), 2.58 (2H, t, J=6.7 Hz, CH$_2$), 3.69 (6H, s, 2×OCH$_3$), 3.71 (3H, s, OCH$_3$), 3.83 (3H, s, OCH$_3$), 3.89 (3H, s, OCH$_3$), 3.95 (3H, s, OCH$_3$), 4.51 (2H, t, J=6.7 Hz, CH$_2$), 5.41 (2H, s, CH$_2$), 6.45 (1H, d, J=12.4 Hz, olefinic H), 6.49 (1H, d, J=12.4 Hz, olefinic H), 6.50 (2H, s, 2'''-H and 6'''-H), 6.82 (1H, d, J=8.3 Hz, H-3''), 6.93-6.97 (2H, m, H-4'' and H-6''), 7.46 (1H, s, H-3'), 7.75 (1H, s, H-6') ppm; $\delta_C$ (100 MHz, CDCl$_3$) 24.3 (CH$_2$), 30.4 (CH$_2$), 51.7 (OCH$_3$), 55.9 (OCH$_3$), 56.0 (OCH$_3$), 56.2 (OCH$_3$), 60.9 (OCH$_3$), 68.2 (CH$_2$), 68.4 (CH$_2$), 105.9 (CH), 109.3 (CH), 109.7 (CH), 111.6 (CH), 115.6 (CH), 123.0 (CH), 129.2 (CH), 129.4 (CH), 129.6, 130.3, 132.6, 137.2, 138.8, 147.0, 147.3, 149.0, 152.9, 154.3, 173.4 (COOCH$_3$) ppm; m/z (FAB) 376 [(M$^+$), 40%].

4-[2'-methoxy-4'-({2''-methoxy-5''-[(Z)-2'''-3''',4''',5'''-trimethoxyphenyl)ethenyl]phenoxy}methyl)-5'-nitrophenoxy]butanoic acid Z-11

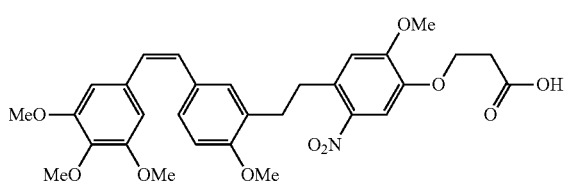

In a foil wrapped flask a suspension of the methyl ester Z-8 (250 mg, 0.42 mmol) in 1M aqueous NaOH (0.84 ml, 0.84 mmol) was prepared. The yellow suspension was then heated at reflux for 40 mins, after which time water (5 cm³) was added. The resulting orange solution was then acidified to pH 1 using conc. HCl and the subsequent yellow precipitate was filtered. The precipitate was purified by recrystallisation from ethanol, which provided the desired compound as a pale yellow solid (214 mg, 81%). m.p. 138° C. Found C, 61.6; H, 5.4; N, 2.3; $C_{30}H_{33}NO_{11}$ requires C, 61.7; H, 5.7; N, 2.4%; $R_f$ 0.10 (SiO$_2$, hexane:EtOAc 1:1 v/v); $\nu_{max}$ (KBr disc)/cm$^{-1}$ 3500-3100 (br), 3000-2800 (m), 1740 (s), 1610, 1580, 1520, 1330, 1280, 1220, 1130, 880; $\delta_H$ (300 MHz, CDCl$_3$) 2.21 (2H, q, J=6.5 Hz, CH$_2$), 2.63 (2H, t, J=6.5 Hz, CH$_2$), 3.67 [6H, s, (OCH$_3$)$_2$], 3.81 (3H, s, OCH$_3$), 3.88 (3H, s, OCH$_3$), 3.93 (3H, s, OCH$_3$), 4.16 (2H, t, J=6.5 Hz, CH$_2$), 5.40 (2H, s, CH$_2$), 6.43 (1H, d, J=12.9 Hz, olefinic CH), 6.47 (2H, s, H-2''' and H-6'''), 6.48 (1H, d, J=12.9 Hz, olefinic H), 6.81 (1H, d, J=7.9 Hz, H-3''), 6.91-6.95 (2H, m, H-4'' and H-6''), 7.45 (1H, s, H-3'), 7.74 (1H, s, H-6') ppm; $\delta_C$ (100 MHz, CDCl$_3$) 24.0 (CH$_2$), 30.1 (CH), 55.9 (OCH$_3$), 56.0 (OCH$_3$), 56.2 (OCH$_3$), 60.9 (OCH$_3$), 68.0 (CH$_2$), 68.4 (CH$_2$), 105.9 (CH), 109.4 (CH), 109.7 (CH), 111.6 (CH), 115.6 (CH), 123.1 (CH), 129.2 (CH), 129.3 (CH), 129.7, 130.3, 132.7, 137.2, 138.8, 146.9, 147.3, 149.0, 152.9, 154.3, 173.5 (COOCH$_3$) ppm; m/z (FAB) 583 [(M$^+$), 100%].

Methyl 4-[2'-methoxy-4'-({2''-methoxy-5''-[(E)-2'''-3''',4''',5'''-trimethoxyphenyl)ethenyl]phenoxy}-methyl)-5'-nitrophenoxy]butanoate E-8

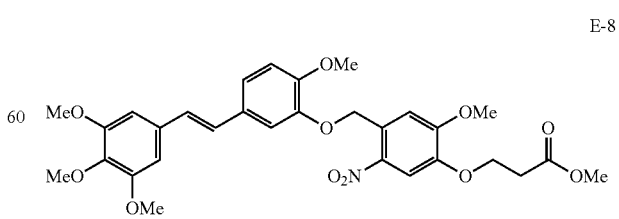

To a suspension of methyl-4-[4'-(bromomethyl)-2'-methoxy-5'-nitrophenoxy]butanoate 7 (400 mg, 1.1 mmol) and trans-CA-4 (280 mg, 0.89 mmol) in anhydrous methanol (10 cm³) was added K'OBu (148 mg, 1.32 mmol). The resulting yellow mixture was stirred at r.t. for 30 mins after which time a yellow precipitate had formed. The precipitate was filtered and recrystallised from methanol furnishing the desired compound E-8 as a pale yellow solid (367 mg, 73%). m.p. 142° C. Found C, 65.5; H, 6.4; N, 2.4; $C_{31}H_{35}NO_{11}$ requires C, 65.6; H, 6.2; N, 2.5%; $R_f$ 0.44 ($SiO_2$, hexane:EtOAc 1:1 v/v); $\nu_{max}$ (KBr disc)/cm⁻¹ 3000-2800 (m), 1730 (s), 1610, 1580, 1520, 1320, 1280, 1220, 1130, 880; $\lambda_{max}$ (MeCN)/nm 219 (ε36612), 243 (ε33655) and 329 (ε41112); $\delta_H$ (300 MHz, $CDCl_3$) 2.20 (2H, p, J=6.8 Hz, $CH_2$), 2.57 (2H, t, J=6.8 Hz, $CH_2$), 3.70 (3H, s, $OCH_3$), 3.86 (3H, s, $OCH_3$), 3.92 [6H, s, $(OCH_3)_2$], 3.93 (3H, s, $OCH_3$), 3.97 (3H, s, $OCH_3$), 4.41 (2H, t, J=6.8 Hz, $CH_2$), 5.61 (2H, s, $CH_2$), 6.73 (2H, s, H-2''' and H-6'''), 6.87 (1H, d, J=16.2 Hz, olefinic H), 6.94 (1H, s, H-3"), 6.95 (1H, d, $J_H$ 16.2 Hz, olefinic CH), 7.11-7.14 (2H, m, H-4" and H-6"), 7.55 (1H, s, H-3'), 7.77 (1H, s, H-6') ppm; $\delta_C$ (100 MHz, $CDCl_3$) 24.4 ($CH_2$), 30.4 ($CH_2$), 51.7 ($OCH_3$), 56.1 [$(OCH_3)_2$], 56.2 ($OCH_3$), 56.3 ($OCH_3$), 61.0 ($OCH_3$), 68.4 (2×$CH_2$), 103.3 (CH), 109.3 (CH), 109.7 (CH), 112.0 (2×CH), 120.7 (CH), 127.2 (CH), 127.5 (CH), 129.9, 130.7, 133.1, 137.8, 138.8, 147.0, 147.8, 149.5, 153.4, 154.5, 173.3 (COOCH₃) ppm; m/z (FAB) 597 [(M⁺), 25%].

4-[2'-methoxy-4'-({2"-methoxy-5"-[(E)-2'''-3''',4''', 5'''-trimethoxyphenyl)ethenyl]phenoxy}methyl)-5'-nitrophenoxy]butanoic acid E-11

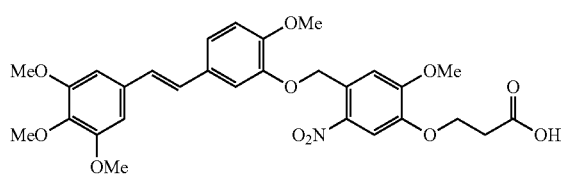

E-11

In a foil wrapped flask a suspension of the methyl ester E-8 (250 mg, 0.42 mmol) in 1M aqueous NaOH (0.84 ml, 0.84 mmol) was prepared. The yellow suspension was then heated at reflux for 40 mins, after which time water (5 cm³) was added. The resulting orange solution was then acidified to pH 1 using conc. HCl and the subsequent yellow precipitate was filtered. The precipitate was purified by recrystallisation from ethanol, which provided the desired compound as a pale yellow solid (234 mg, 97%). m.p. 177° C. Found C, 62.0; H, 5.8; N, 2.5; $C_{30}H_{33}NO_{11}$ requires C, 61.7; H, 5.7; N, 2.4%; $R_f$ 0.15 ($SiO_2$, hexane:EtOAc 1:1 v/v); $\nu_{max}$ (KBr disc)/cm⁻¹ 3500-3100 (br), 3000-2800 (m), 1710 (m), 1610, 1580, 1520, 1330, 1280, 1220, 1130; $\delta_H$ (300 MHz, $CDCl_3$) 2.25 (2H, q, J=6.7 Hz, $CH_2$), 2.66 (2H, t, J=6.7 Hz, $CH_2$), 3.90 (3H, s, $OCH_3$), 3.95 (3H, s, 2×$OCH_3$), 3.96 (3H, s, $OCH_3$), 4.00 (3H, s, $OCH_3$), 4.19 (2H, t, J=6.7 Hz, $CH_2$), 5.64 (2H, s, CH), 6.76 (2H, s, H-2''' and H-6'''), 6.93-6.98 (3H, m), 7.14-7.16, (2H, m, H-4" and H-6"'), 7.59 (1H, s, H-3'), 7.82 (1H, s, H-6') ppm; $\delta_C$ (100 MHz, $CDCl_3$) 24.0 ($CH_2$), 30.0 ($CH_2$), 56.1 (2×$OCH_3$), 56.2 ($OCH_3$), 56.3 ($OCH_3$), 61.0 (OCH), 68.1 ($CH_2$), 68.2 ($CH_2$), 103.3 (2×CH), 109.3 (CH), 109.8 (CH), 112.0 (CH), 120.7 (CH), 127.2 (CH), 127.5 (CH), 130.1, 130.7, 133.1, 137.9 139.2, 146.8, 147.8, 149.5, 153.4, 154.8, 177.4 (COOH) ppm; m/z (FAB) 583 [(M⁺), 70%].

4-[2'-methoxy-4'-({2"-methoxy-5"-[(E)-2'''-3''',4''', 5'''-trimethoxyphenyl)ethenyl]phenoxy}methyl)-5'-nitrophenoxy]butanoic acid (potassium salt) E-12

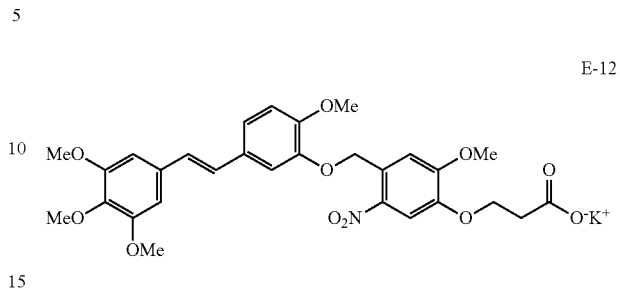

E-12

To a suspension of the butanoic acid E-11 (250 mg, 0.43 mmol) in methanol (3 cm³) was added K'OBu [0.43 cm³, 0.43 mmol, (1 M methanolic solution)]. The resulting clear yellow solution was stirred at r.t. for 5 minutes before being concentrated in vacuo to provide a pale brown solid (0.26 mg, 97%).

Example 8

Photochemical Cleavage and Isomerisation

Methyl 4-[2'-methoxy-4'-({2"-methoxy-5"-[(E)-2'-3''',4''',5'''-trimethoxyphenyl)ethenyl] phenoxy}methyl)-5'-nitrophenoxy]butanoate, E-8

In a 400 cm³ photochemical reaction vessel, $N_2$ was bubbled through distilled benzene (300 cm³) for 30 mins. Following the degassing procedure, compound E-12 (300 mg, 0.5 mmol) was added to the benzene and allowed to dissolve. The colourless solution was then irradiated using a 400 W medium pressure Hg lamp for a total of 20 mins. Aliquots were removed from the reaction vessel at specific time points throughout the mins (0, 0.5, 1.0, 1.5, 2.0, 3.0, 4.0, 5.0, 7.5, 10.0, 12.5, 15.0, 17.5, 20.0 mins). Two aliquots were removed from the reaction vessel at each time point, one sample (0.5 cm³) was used for HPLC analysis (cyanopropyl column; mobile phase 95:5 hexane:IPA; flow rate 0.5 ml min⁻¹; lamp 245 nm), whilst the other sample (10 cm³) was concentrated in vacuo and used to determine the $IC_{50}$ at that time point. After irradiation for 20 mins the reaction mixture was yellow/orange in colour.

The following compound retention times were observed:

| | |
|---|---|
| Trans-CA-4 | 23.35 mins |
| Cis-CA-4 | 11.07 mins |
| Coupled trans-CA-4 E-8 | 43.89 mins |
| Coupled cis-CA-4 E-8 | 26.42 mins |

Example 9

Photochemical Isomerization of Combrestatatin A-4 and Derivatives

We detail the study of the trans to cis isomerisation of CA-4 herein. A solution of trans-CA-4 (200 mg, 0.63 mmol) in freshly distilled and degassed benzene (400 cm³), prepared by bubbling through Ar for 2 hours prior to use, was irradiated using a 400 W medium pressure Hg lamp for a total of 20 mins. Aliquots were removed at regular intervals for GC analysis (180-280° C. at 5° C. min$^{-1}$; pressure program 195-225 kPa at 1.5 kPa min$^{-1}$; on a SE54 column).

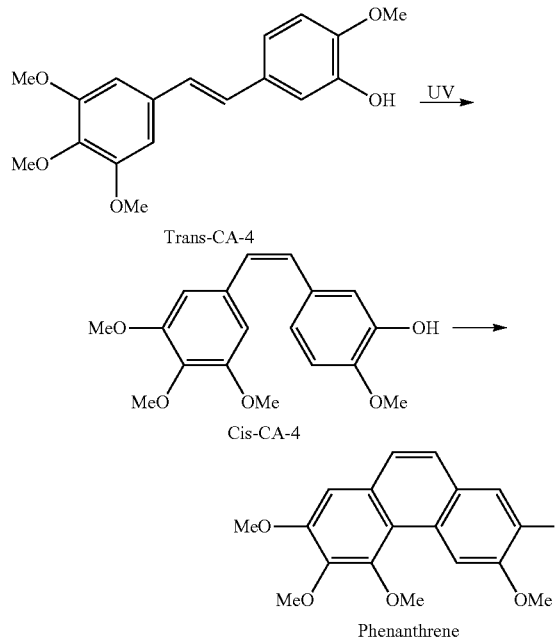

The results of GC analysis of the mixture are summarized in Table 3. Table 4 shows the retention times, by GC for the individual components of the reaction mixture.

TABLE 3

| Time (mins) | % trans-stilbene | % cis-stilbene | % phenanthrene |
| --- | --- | --- | --- |
| 0 | 100 | 0 | 0 |
| 0.5 | 100 | 0 | 0 |
| 1.5 | 100 | 0 | 0 |
| 3.0 | 87 | 13 | 0 |
| 5.0 | 69 | 31 | 0 |
| 6.5 | 55 | 45 | 0 |
| 8.0 | 53 | 47 | 0 |
| 10.0 | 44 | 53 | 0 |
| 12.5 | 32 | 68 | 0 |
| 15.0 | 29 | 71 | 0 |
| 17.5 | 22 | 74 | 4 |
| 20.0 | 23 | 73 | 4 |

TABLE 4

| Component | Retention time (mins)* |
| --- | --- |
| trans-CA-4 | 20.32 |
| cis-CA-4 | 15.42 |
| CA-4 phenanthrene derivative 1 | 19.00 |

*G.C. conditions; 180-280° C. @ 5° C. min$^{-1}$, 195-225 kPa @ 1.5 kPa min$^{-1}$, SE 54 column.

Table 5 shows the outcome of photoisomerisation of trans-CA-4 (99.7% E) and the corresponding IC$_{50}$ values. The cytotoxicity (IC$_{50}$ value) of the reaction mixture at each time point is shown in Table 3, showing an impressive increase in the cytotoxicity of the mixture over time.

The most exciting observation is that the IC$_{50}$ at time zero is 4000 nM and after just half a minute it has decreased by more than 10 fold. This illustrates that the isomerization is rapid and also highlights just how potent cis-CA-4 is compared with trans-CA-4 since just 2.0% of cis-CA-4 present results in such a dramatic increase in cytotoxicity. The thousand-fold increase in activity obtained after six minutes, clearly shows that the process displays great potential.

TABLE 5

| Time (mins) | % trans | % cis | % phenanthrene | IC$_{50}$ (K562) (nM) |
| --- | --- | --- | --- | --- |
| 0 | 99.7 | 0.3 | 0 | 4000 |
| 0.5 | 98.0 | 2.0 | 0 | 310 |
| 1.0 | 96.1 | 3.9 | 0 | 530 |
| 1.5 | 93.7 | 6.3 | 0 | 50 |
| 2.0 | 92.7 | 7.3 | 0 | 20 |
| 3.0 | 74.3 | 25.7 | 0 | 12 |
| 4.0 | 62.3 | 37.3 | 0 | 9 |
| 5.0 | 52.1 | 47.9 | 0 | 10 |
| 7.5 | 40.2 | 56.6 | 1.4 | 3 |
| 10.0 | 34.0 | 63.1 | 2.9 | 6 |
| 12.5 | 32.2 | 64.4 | 3.4 | 4 |
| 15.0 | 31.7 | 64.6 | 3.7 | 1 |
| 17.5 | 30.8 | 65.1 | 4.1 | 3 |
| 20.0 | 30.6 | 65.7 | 3.7 | 2 |

Previously, the isomerisation study had been performed ex situ, i.e. in a photochemical reactor. However, it was necessary to illustrate the potential of the process as a real therapy by repeating the isomerizaton in the presence of the cancer cells i.e. in situ. Therefore, K562 cells were dosed with a known concentration of trans-CA-4, the resulting solutions were then irradiated using an ultra violet lamp consisting of 2×7 W ultra violet tubes for given lengths of time. Following irradiation, the cells were incubated in the normal way and the IC$_{50}$ values were determined. A series of control experiments were performed simultaneously to verify that the results obtained (illustrated in Table 6) were in fact due to the isomerisation process occurring and not due to the effect of the ultraviolet radiation. Table 6 shows that the same pattern of results is obtained. However, the decrease in the IC$_{50}$ value is now more rapid.

The experiment convincingly supports the results derived from the ex situ study and we are able to show that the trans to cis isomerisation is occurring in both circumstances, and more importantly is causing a rapid and significant increase in the cytotoxicity of the system. Due to the speed with which the process was occurring the experiment was repeated and monitored every 5 seconds in the first minute of irradiation. The results are shown in Table 7. It can be seen that after just 5 seconds there is a greater than 15 fold reduction in the IC$_{50}$ and after a further 40 seconds a single nanomolar figure IC$_{50}$ value is reached.

TABLE 6

| Time/mins | IC$_{50}$ K562 nM |
| --- | --- |
| 0 | 1200 |
| 1 | 3.6 |
| 2 | 2.9 |
| 3 | 1.7 |
| 4 | 4.4 |
| 5 | 2.7 |
| 6 | 2.9 |
| 7 | 1.9 |
| 8 | 3.0 |
| 9 | 2.5 |
| 10 | 2.6 |
| 12.5 | 2.4 |
| 15.0 | 2.0 |
| 17.5 | 1.7 |
| 20.0 | 2.7 |

TABLE 7

| Time/secs | IC$_{50}$ K562 nM |
|---|---|
| 0 | 580 |
| 5 | 35 |
| 10 | 40 |
| 15 | 20 |
| 20 | 18 |
| 25 | 17 |
| 30 | 15 |
| 35 | 11 |
| 40 | 11 |
| 45 | 9 |
| 50 | 9 |
| 55 | 9 |
| 60 | 8 |

Example 10

Synthesis of Trans-CA-4 Bearing a Photocleavable Group

We next demonstrate the potential use of light to trigger the release of CA-4 from a variety of non-toxic CA-4 derivatives. By way of example, two types of reaction were employed:

(1) Release of CA-4 from a trans-CA-4 derivative with E to Z isomerization.

(2) Release of CA-4 from a photolabile cis-CA-4 derivative.

As in some applications in the prior art, the insolubility of CA-4 in water results in clinical difficulties, it would be advantageous to utilize a photocleavable group to impart water solubility to the system.

We first considered the fate of a trans-CA-4 derivative (2) bearing a photocleavable water solubilising (PCWS) group (see the scheme below). When irradiated with ultraviolet light, two events can occur; (i) the PCWS group can be cleaved and (ii) trans to cis isomerisation can take place, (but perhaps not in that order). The overall effect of these transformations should be a dramatic increase in cytotoxicity.

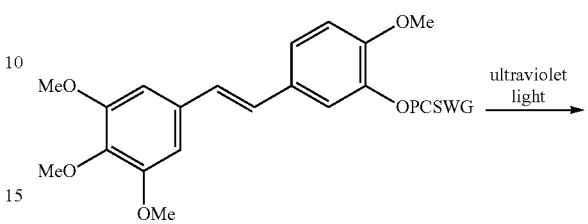

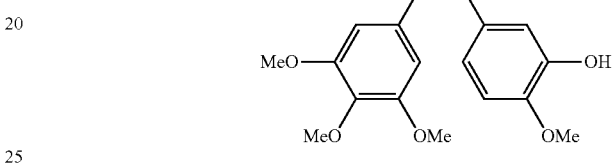

It became apparent that whilst there are examples of the use of photocleavable groups in medical applications there are no examples of their use in this context. To demonstrate the validity of this approach we used an ortho-nitrobenzyl derivative as a prototypical photocleavable group. A vanillin based compound, developed by Holmes et al. (C. Holmes, *J. Org. Chem.*, 1997, 62, 2370.) as a solid phase linker, was used as a template for our photocleavable group. The synthetic strategy to the coupling agent 7 is outlined in the following scheme.

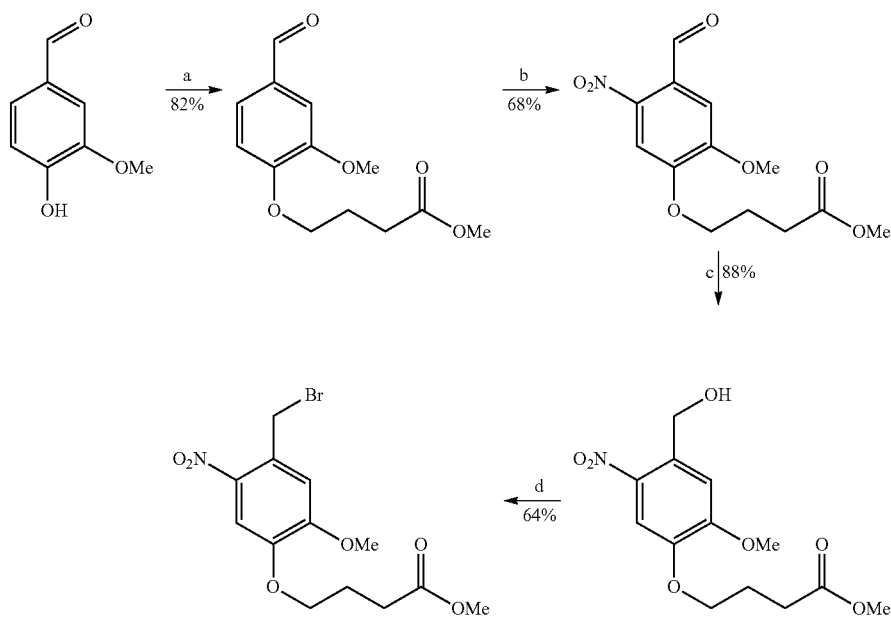

a) Methyl-4-bromobutyrate, K$_2$CO$_3$, DMF;
b) HNO$_3$, DCM, -5° C.;
c) NaBH$_4$, THF,
d) PBr$_3$, DCM.

The next step was to couple the benzyl bromide 7 to trans-CA-4. The reaction gave the desired product E-8 in a 73% yield, as illustrated below. E-8 precipitated out of solution as the reaction to place and was subsequently filtered and purified by recrystallisation. The coupling reaction was repeated using cis-CA-4 as the substrate—the reaction proceeded in a 69% yield.

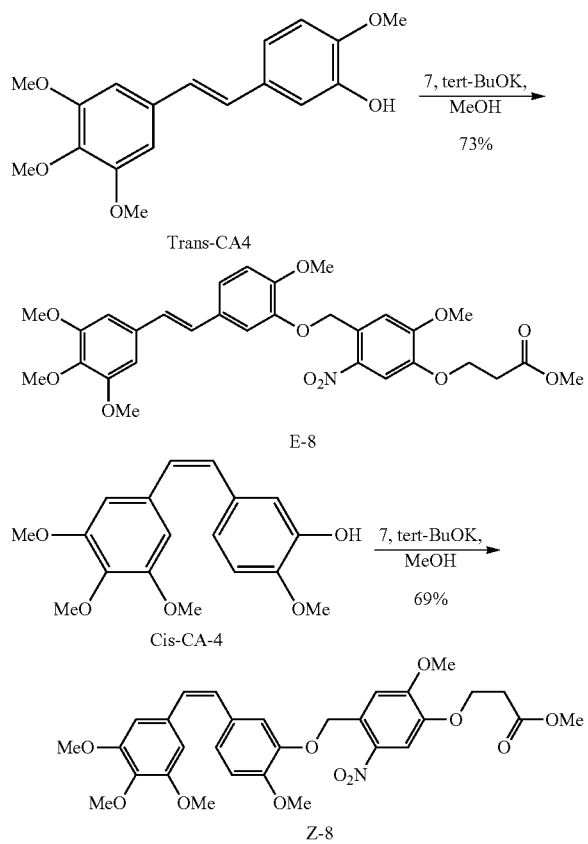

As with the trans to cis photoinduced isomerisation study coupled trans-CA-4 was dissolved in benzene and the resulting solution was irradiated for a total of 20 minutes with aliquots removed at given time points to determine the isomeric ratios and the $IC_{50}$ value. The results obtained are detailed in Table 8.

TABLE 8

| Time/mins | % coupled trans-CA-4 (E-8) | % trans-CA-4 | % cis-CA-4 | $IC_{50}$ K562 (nM) |
|---|---|---|---|---|
| 0 | 100 | — | — | >150000 |
| 0.5 | 93 | 7 | — | 14580 |
| 1.0 | 88 | 8 | 4 | 450 |
| 1.5 | 80 | 12 | 8 | 90 |
| 20. | 72 | 19 | 9 | 59 |
| 3.0 | 62 | 27 | 11 | 14 |
| 4.0 | 61 | 31 | 8 | 12 |
| 5.0 | 53 | 37 | 10 | 8 |
| 7.5 | 42 | 45 | 13 | 4 |
| 10.0 | 34 | 47 | 19 | 6 |
| 12.5 | 20 | 35 | 45 | 2 |
| 15.0 | Unable to calculate* | | | 2 |
| 17.5 | Unable to calculate* | | | 4 |
| 20.0 | Unable to calculate* | | | 3 |

The results show that the photocleavage of trans-CA-4 is the first event to occur, followed soon after by the isomerisation of trans-CA-4 to cis-CA-4. This process is accompanied by an even more dramatic increase in the cytotoxicity than was seen previously, this is largely because E-8 is much less cytotoxic than trans-CA-4, in fact it is 5 times less cytotoxic. This is highly beneficial if E-8 were to be used as a CA-4 prodrug. These results also highlight the speed with which the process occurs. After just 5 minutes exposure to ultra violet light the $IC_{50}$ value has fallen to single nanomolar figures, with slightly more than 50% of the coupled starting material remaining and some 10% cis-CA-4 present.

Once again it was desirable to investigate the effect of the coupled trans-CA-4, E-8 upon irradiation in the presence of cancer cells. Therefore, K562 cells were dosed with a known concentration of coupled trans-CA-4 E-8 and subsequently exposed to ultra violet radiation for specific lengths of time and the $IC_{50}$ value determined. As with the previous in situ experiment a series of control experiments were performed simultaneously to verify that any positive results obtained were due to the effect of ultra violet light on the drug candidate and not its effect on the cells. These consisted of i) exposing K562 cells only (i.e. cells which were not dosed with any potential drug candidate) to ultra violet light, ii) preventing K562 cells dosed with drug candidate from being exposed to ultra violet light, and iii) preventing K562 cells only (i.e. cells which were not dosed with any potential drug candidate) from being exposed to ultra violet light. In all three control experiments no cytotoxic effect was observed. The results of the main experiment are illustrated in Table 9. It is apparent that the same general trend, with respect to the $IC_{50}$ values is seen in both the ex situ and the in situ experiments.

TABLE 9

| Time/Mins | $IC_{50}$ K562 (nm) |
|---|---|
| 0 | >100000 |
| 0.5 | 1540 |
| 1 | 450 |
| 1.5 | 250 |
| 2 | 130 |
| 3 | 40 |
| 4 | 11 |
| 5 | 9 |
| 7.5 | 5 |
| 10 | 2 |
| 12.5 | 3 |
| 15 | 3 |
| 17.5 | 2 |
| 20 | 2 |

We needed to demonstrate that the photo by-product, the nitrosobenzaldehyde, 10 did not possess any cytotoxicity and therefore was not contributing to the results obtained for the photoactivation of coupled trans-CA-4. The synthesis of the nitroso compound, 10 was achieved by exposing compound 9 to ultra violet light for 10 minutes and the desired compound was isolated from the resulting reaction mixture via column chromatography (see the scheme below). The compound 10 lacked significant cytotoxicity.

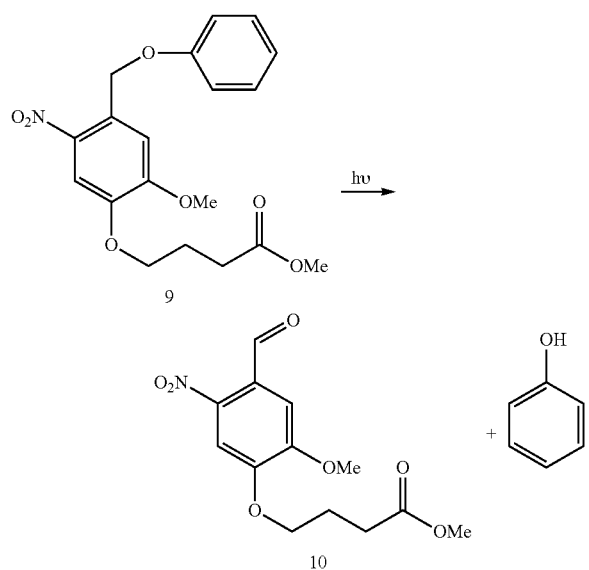

Having convincingly established the feasibility of prodrug photoactivation, the final objective was to render the coupled trans-CA-4 compound, E-8 water-soluble. A water soluble prodrug of CA-4 would clearly have clinical potential. Therefore, a water-soluble derivative was synthesised in an attempt to overcome this problem. The water-soluble derivative was prepared from the methyl ester, E-8 by a simple hydrolysis reaction using NaOH in ethanol. However, due to purification problems the carboxylic acid, E-11 was isolated and subsequently deprotonated with K'OBu, the water-soluble salt was isolated using ion-exchange chromatography.

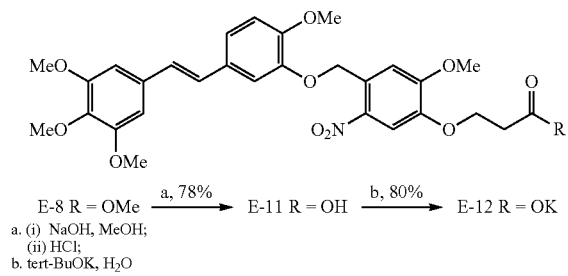

The in situ study of the water-soluble derivative of trans-CA-4 was performed in the same manner as those described previously and the results can be seen in Table 10. The results obtained suggest that the water-soluble derivative, E-12 behaves in a similar fashion as the methyl ester derivative, E-8 when irradiated with ultra violet light in the presence of cancer cells. The $IC_{50}$ values obtained are similar to those obtained for the in situ study of the methyl ester derivative, E-8.

TABLE 10

| Time/Mins | $IC_{50}$ K562 (Nm) |
|---|---|
| 0 | >50000 |
| 0.5 | 1010 |
| 1 | 410 |
| 1.5 | 300 |
| 2 | 160 |
| 3 | 50 |
| 4 | 58 |
| 5 | 46 |
| 7.5 | 22 |
| 10 | 16 |
| 12.5 | 12 |
| 15 | 10 |
| 17.5 | 9 |
| 20 | 8 |

Example 11

Further Biological Experiments

The effect of compounds 97-64H and 97-96 (quinone compound) was tested on H460 human lung xenograft grown subcutaneously by injecting equitoxic doses of the compounds (0.75×MTD). Twenty four hours following injection (i.p.) both compounds caused extensive damage to the tumours which was consistent with necrosis caused by destruction of vasculature.

The results from testing compounds of the invention in cell based assays are reported in Tables 12 to 27 below.

The references cited herein are incorporated by reference.

TABLE 11

| Compound | P388 $1C_{50}$ (µM) | A2780 $1C_{50}$ (µM) | H460 $1C_{50}$ (µM) | K562 (µM) | Tub Ass $1C_{50}$ (µM) | Colchicine % Inhibition | HUVEC $1C_{50}$ (µM) | Permeability |
|---|---|---|---|---|---|---|---|---|
| Comb A-4 (1) | 0.0026 | 0.00072 | 1.51 | | 2.4 | 12 | 0.001 | 7.1, 6.9 |
| 97-64H | 0.000489 | 0.00366 | | | <1.25, 12.5 | 79, 70 | .0024 | 5.8 |
| 97-64L | 0.171 | 0.113 | | | >100 | 43 | NT | 1.0 |
| 97-65 | 0.18 | 0.095 | | | 100 | NT | 0.35 | 3.4 |
| 96-188 | 0.32 | .081 | | | NT | NT | | |
| 96-167 | 0.0008 | 0.00037 | | | 9 | 3.8 | 0.04 | 5.5 |
| 97-07 | 0.0023 | 0.00147 | 2.78 | | 10 | 6.6, 12.3 | | |
| 97-13H | 0.0326 | 0.0179 | .032-.035 | | >100 | 84.2 | 0.045 | 4.3, 3.2 |
| 98-21 | .000935 | .00066 | | | <1.25 | 1.4 | 0.0095 | 4.5 |
| 97-96 | 0.57 | 0.19 | .038 | | <1.25 | 82, 24 | 0.23, 0.22 | 2.2 |
| 98-23 | 2.18 | 2.15 | 4.37 | | NT | NT | | |
| 98-35H | .00328 | .00144 | | | 6.25 | 5 | 0.016 | 7.4 |
| 98-29 | 0.45 | 0.38 | | | >100 | 53 | 0.43 | 3.9 |
| 99-03H | 0.19 | 0.12 | | 0.06 | 60 | | | |
| 00-82 | | .06 | | 0.05 | 7.2 | 39.5 | | |
| 00-105 | | | | 0.02 | >100 | 3.6 | | |
| 17a | | | | 0.2 | | | | |
| 17b | | | | 6 | | | | |
| 19 | | | | 0.04 | 1.8 | | | |

TABLE 11-continued
| Compound | P388 1C$_{50}$ (μM) | A2780 1C$_{50}$ (μM) | H460 1C$_{50}$ (μM) | K562 1C$_{50}$ (μM) | Tub Ass 1C$_{50}$ (μM) | Colchicine % Inhibition | HUVEC 1C$_{50}$ (μM) | Permeability |
|---|---|---|---|---|---|---|---|---|
| 20 | 7 | | | 1.8 | | | | |
| 23a | | | | 0.1 | | | | |
| 23b | | | | 0.79 | | | | |
| 27 | | | | 9 | | | | |
| 28 | | | | 0.021 | 1.5 | | | |
| 31a | | | | 0.018 | 7.5 | | | |
| 32a | | | | 0.044 | 18 | | | |
| 45 | | | | 0.12 | 1.8 | | | |
NT = NOT TESTED;
'H' COMPOUNDS ARE CIS, 'L' COMPOUNDS ARE TRANS. Stilbenes synthesised by either Wittig or 2-step synthesis routes. Quinone synthesised as in Section 9.
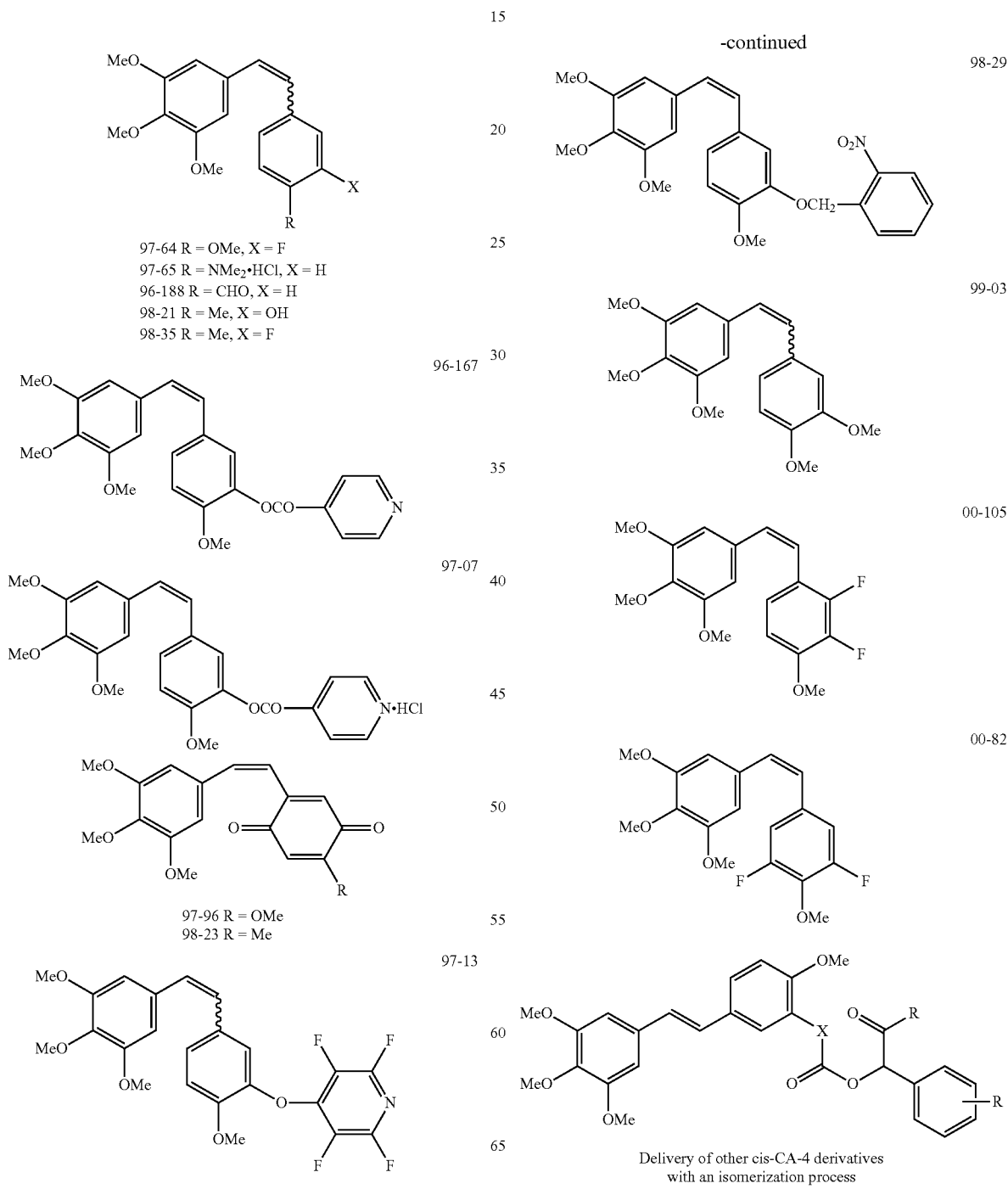
Delivery of other cis-CA-4 derivatives with an isomerization process

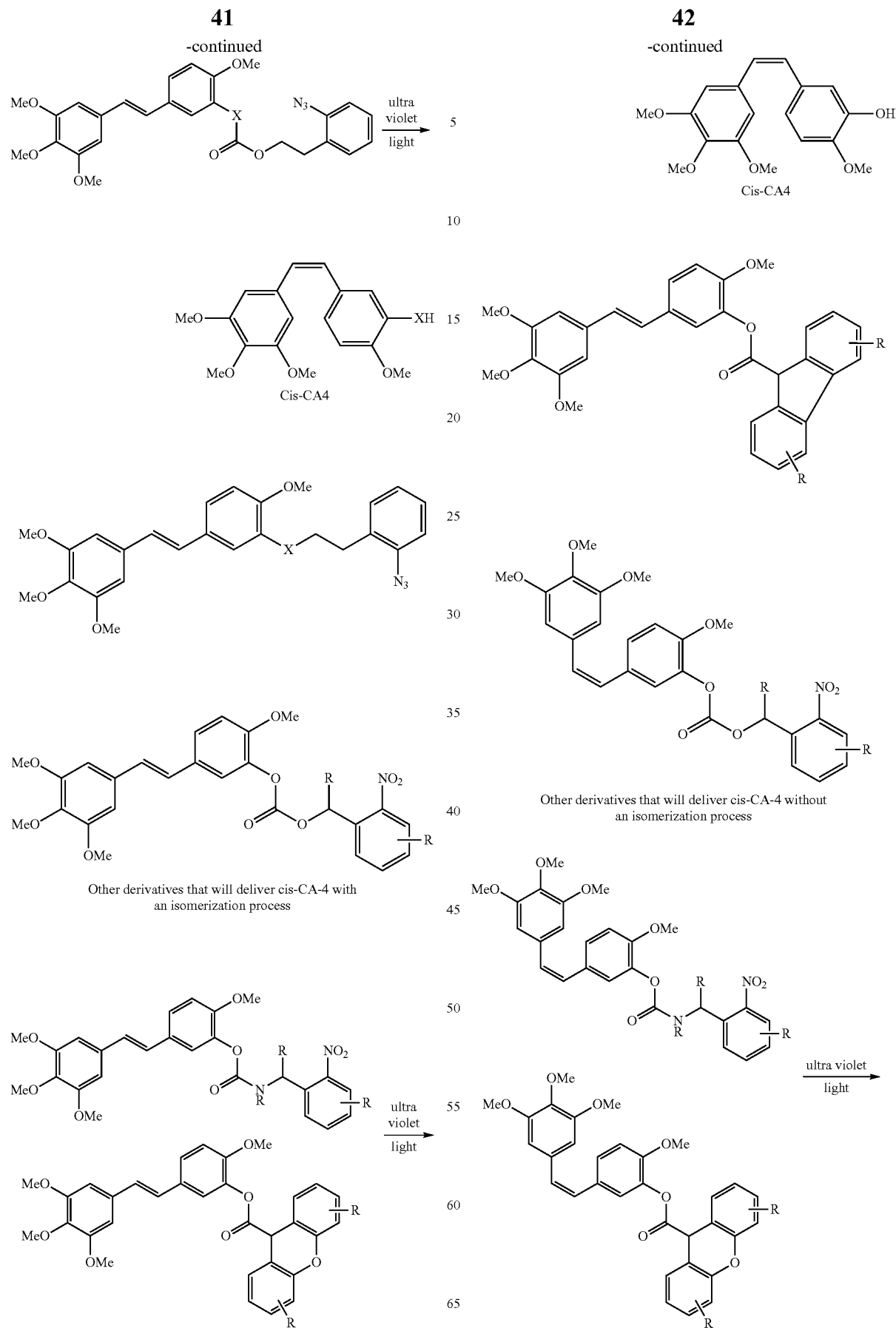

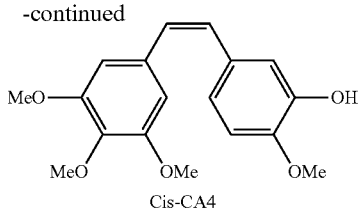

Cis-CA4

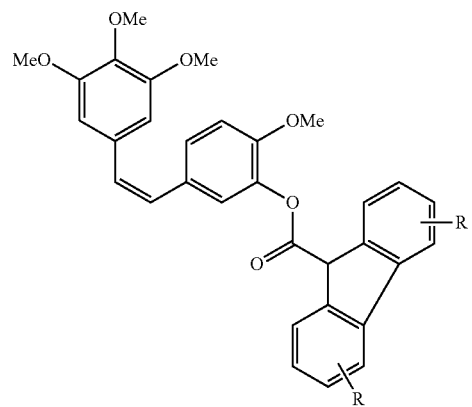

X = O or NH

TABLE 12

Biological activity of stilbenes with 3,4,5-trimethoxy substitution on the A ring

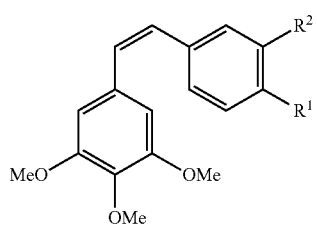

| Compound number | R₂ | R₁ | Config | MTT (P388) IC$_{50}$ (μM) | MTT (K562) IC$_{50}$ (μM) | MA IC$_{50}$ (μM) | CD IC$_{50}$ (μM) |
|---|---|---|---|---|---|---|---|
| CA4 (15) | OH | OMe | Z | 0.003 | 0.001 | 0.175 | 3 |
| 32 | H | OMe | Z | ND | 0.004 | 0.2 | 5.5 |
| 90 | F | OMe | Z | ND | 0.01 | 0.085 | 2.8 |
| 93 | Br | OMe | Z | ND | 0.001 | 0.4 | 10 |
| 96 | | | E | ND | 7.83 | >10 | >25 |
| 101 | OH | H | Z | 0.3 | 0.14 | >10 | >25 |
| 102 | | | E | 34 | 22 | >10 | >25 |
| 103 | Me | Me | Z | 0.1 | 0.04 | 2 | >25 |
| 104 | | | E | 20 | 35.8 | >10 | >25 |

TABLE 13

Growth inhibition studies using HUVEC

| Drug | HUVEC IC$_{50}$ (μM) |
|---|---|
| CA4 (15) | 0.0026 |
| 90 | 0.004 |
| 32 | 0.006 |
| 93 | 0.067 |

TABLE 14

Biological activity of stilbenes with 3,4,5-trimethyl substitution on the A ring

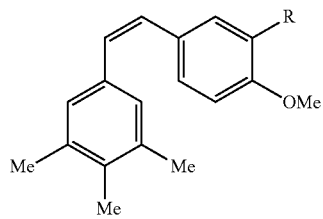

| Compound number | R | MTT (K562) IC$_{50}$ (μM) | MA IC$_{50}$ (μM) | CD IC$_{50}$ (μM) |
|---|---|---|---|---|
| Combretastatin A-4 (15) | | 0.001 | 0.175 | 3 |
| 117 | H | 0.31 | 0.650 | >25 |
| 120 | F | 0.14 | 0.700 | 10 |
| 133 | OH | 0.020 | 0.120 | 10 |

TABLE 15

Growth inhibition studies using HUVECs

| Drug | HUVEC IC$_{50}$ (μM) |
|---|---|
| 117 | >1 |
| 120 | 0.46 |
| 133 | 0.05 |

TABLE 16

K562 cell cycle analysis

| Drug | % of cells with DNA content <2n | % of cells in $G_0$-$G_1$ | % of cells in S phase | % of cells in $G_2$-M |
|---|---|---|---|---|
| 117 | 15 | 3 | 10 | 87 |
| 120 | 23 | 6 | 17 | 77 |
| 133 | 6 | 3 | 6 | 91 |

The % of cells in $G_0$-$G_1$, S phase, and $G_2$-M columns represent % of cells with DNA content = 2n or >2n.

TABLE 17

Biological activity of stilbenes with 3,4-dimethyl substitution on the A-ring

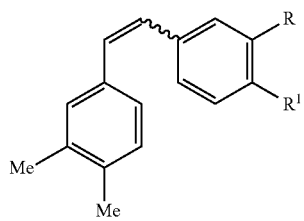

| Compound number | R | $R^1$ | Config | MTT (P388) $IC_{50}$ (μM) | MTT (K562) $IC_{50}$ (μM) | MA $IC_{50}$ (μM) | CD $IC_{50}$ (μM) |
|---|---|---|---|---|---|---|---|
| Combretastatin A-4 (15) | | | Z | 0.003 | 0.001 | 0.175 | 3 |
| 137 | H | Me | Z | 2 | 3.4 | >10 | >25 |
| 138 | | | E | 17 | >50 | >10 | >25 |
| 139 | $NO_2$ | OMe | Z | 20 | 1.8 | >10 | >25 |
| 140 | | | E | >50 | 24 | >10 | >25 |
| 141 | H | OMe | Z | 4.9 | 1.6 | >10 | >25 |
| 142 | | | E | 20.5 | >50 | >10 | >25 |
| 143 | Br | OMe | Z | 2.5 | 1.15 | >10 | >25 |
| 144 | | | E | >50 | >50 | >10 | >25 |
| 146 | OH | OMe | Z | 0.4 | 0.07 | 3.09 | 12.5 |
| 147 | F | OMe | Z | 1.7 | 0.09 | 6.57 | >25 |
| 148 | | | E | 36 | 2.5 | >10 | >25 |
| 149 | F | Me | Z | 7.2 | 0.39 | >10 | >25 |
| 150 | | | E | 40 | >50 | >10 | >25 |
| 151 | $NO_2$ | Me | Z | 9.7 | 1.5 | >10 | >25 |
| 152 | | | E | >50 | >50 | >10 | >25 |

TABLE 18

K562 cell cycle analysis

| Drug | % of cells with DNA content <2n | % of cells in $G_0$-$G_1$ | % of cells in S phase | % of cells in $G_2$-M |
|---|---|---|---|---|
| Combretastatin A-4 (15) | 7 | 3 | 6 | 92 |
| 146 | 31 | 8 | 27 | 65 |
| 147 | 28 | 10 | 33 | 57 |

The % of cells in $G_0$-$G_1$, S phase, and $G_2$-M columns represent % of cells with DNA content = 2n or >2n.

TABLE 19

Biological activity of stilbenes with 3,4,5-triethoxy substitution on the A-ring

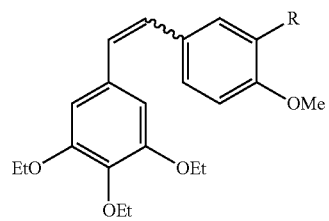

| Compound number | R | Config | MTT (K562) $IC_{50}$ (μM) | MA $IC_{50}$ (μM) | CD $IC_{50}$ (μM) |
|---|---|---|---|---|---|
| Combretastatin A-4 (15) | | Z | 0.001 | 0.175 | 3 |
| 247 | Br | Z | 0.6 | >10 | >25 |
| 248 | | E | >50 | >10 | >25 |

TABLE 19-continued

Biological activity of stilbenes with 3,4,5-triethoxy substitution on the A-ring

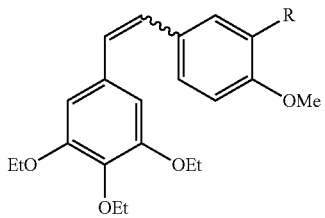

| Compound number | R | Config | MTT (K562) IC$_{50}$ (μM) | MA IC$_{50}$ (μM) | CD IC$_{50}$ (μM) |
|---|---|---|---|---|---|
| 249 | H | Z | 0.5 | >10 | >25 |
| 250 |   | E | >50 | >10 | >25 |
| 251 | F | Z | 0.044 | 1.25 | >25 |
| 252 |   | E | >50 | >10 | >25 |
| 253 | OH | Z | 0.018 | 0.50 | 15.5 |
| 254 |   | E | 0.2 | >10 | >25 |
| 255 | Br | Z | 0.6 | >10 | >25 |
| 256 |   | E | >50 | >10 | >25 |
| 257 | Cl | Z | 0.45 | >10 | >25 |
| 258 |   | E | 7 | >10 | >25 |

TABLE 20

Growth inhibition studies using HUVECs

| drug | HUVEC IC$_{50}$ (μM) |
|---|---|
| 253 | 0.05 |
| 251 | 0.19 |

TABLE 21

K562 cell cycle analysis

| | | % of cells with DNA content = 2n or >2n | | |
|---|---|---|---|---|
| Drug | % of cells with DNA content <2n | % of cells in G$_0$-G$_1$ | % of cells in S phase | % of cells in G$_2$-M |
| 253 | 4 | 3 | 6 | 92 |
| 251 | 24 | 7 | 18 | 75 |

TABLE 22

Biological activity of stilbenes with substitution on the olefinic bond

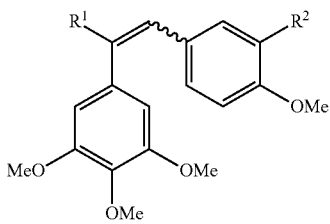

| Compound number | R$^1$ | R$^2$ | Config | MTT (K562) IC$_{50}$ (μM) | MA IC$_{50}$ (μM) | CD IC$_{50}$ (μM) |
|---|---|---|---|---|---|---|
| Combretastatin A-4 (15) | | | Z | 0.001 | 0.175 | 3 |
| 208 | Me | OTBDMS | Z | 0.2 | 1.5 | >25 |
| 209 | | | E | 6 | >10 | >25 |
| 210 | Me | OH | Z | 0.04 | 0.13 | 6 |
| 211 | | | E | 0.7 | >10 | >25 |
| 213 | Me | H | Z | 0.1 | 1.3 | >25 |
| 214 | | | E | 0.8 | >10 | >25 |
| 217 | Et | OTBDMS | Z | 0.5 | >10 | >25 |
| 218 | | | E | 3.4 | >10 | >25 |
| 219 | Et | OH | Z | 0.12 | 0.13 | >25 |
| 220 | | | E | 4 | >10 | >25 |
| 80 | CO$_2$H | OH | E | >50 | >10 | >25 |
| 81 | CO$_2$Me | OH | E | >50 | >10 | >25 |
| 82 | CH$_2$OH | OH | E | >50 | >10 | >25 |

TABLE 23

Growth inhibition studies using HUVECs

| Drug | HUVEC IC$_{50}$ (μM) |
|---|---|
| 210 | 0.09 |
| 213 | 0.35 |
| 219 | 0.22 |

TABLE 24

K562 cell cycle analysis on double bond substituted analogues

| | | % of cells with DNA content = 2n or >2n | | |
|---|---|---|---|---|
| Drug | % of cells with DNA content <2n | % of cells in G$_0$-G$_1$ | % of cells in S phase | % of cells in G$_2$-M |
| 210 | 23 | 5 | 22 | 73 |
| 213 | 23 | 5 | 21 | 73 |
| 219 | 24 | 7 | 19 | 74 |

TABLE 25

Biological activity of stilbenes with substitution on the double bond

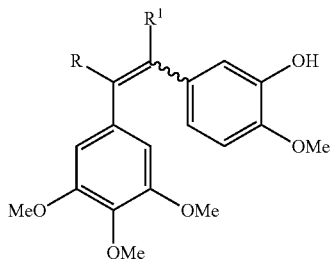

| Compound number | Config | R | $R^1$ | MTT (P388) $IC_{50}$ (μM) | MTT (K562) $IC_{50}$ (μM) | MA $IC_{50}$ (μM) | CD $IC_{50}$ (μM) |
|---|---|---|---|---|---|---|---|
| 200 | E | H | Me | 7 | 2 | 9 | >25 |
| 210 | Z | Me | H | ND | 0.04 | 0.13 | 6 |
| 211 | E | Me | H | ND | 0.7 | >10 | >25 |

TABLE 26

Biological activity of monofluoro prodrug precursors

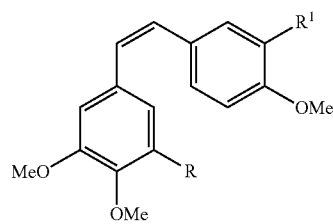

| Compound number | R | $R^1$ | Config | MTT (K562) $IC_{50}$ (μM) | MA $IC_{50}$ (μM) | CD $IC_{50}$ (μM) |
|---|---|---|---|---|---|---|
| Combretastatin A-4 (15) | | | Z | 0.001 | 0.175 | 3 |
| 240 | OTBDMS | F | Z | 0.5 | >10 | >25 |
| 241 | | | E | 10 | >10 | >25 |
| 242 | OH | F | Z | 0.02 | 1.25 | 9 |
| 243 | | | E | 5 | >10 | >25 |
| 90 | OMe | F | Z | 0.01 | 0.085 | 2.8 |
| 18 | OH | OH | Z | 0.04[a] | 4-5 | 22 |

[a] L1210 murine leukaemia cell line

TABLE 27

K562 cell cycle analysis

| Drug | % of cells with DNA content <2n | % of cells in $G_0$-$G_1$ | % of cells in S phase | % of cells in $G_2$-M |
|---|---|---|---|---|
| 242 | 29 | 7 | 22 | 71 |
| 90 | 16 | 5 | 16 | 79 |

% of cells with DNA content = 2n or >2n

21. The compound of claim 1, having the formula:
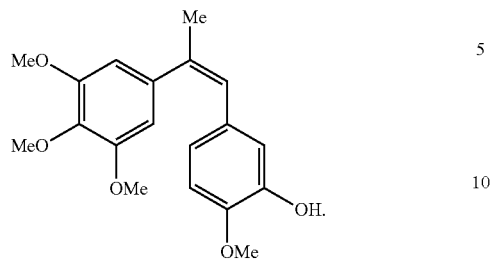

What is claimed is:

1. A compound represented by the structural formula:

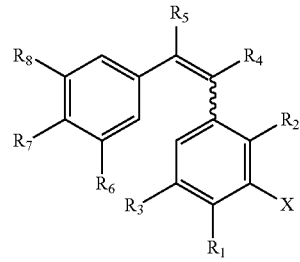

wherein:
the zigzag line indicates that the compound can be cis or trans;
X is selected from hydroxyl, nitro, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl or O-ester;
$R_1$ is selected from alkyl, CHO, alkoxy, $NH_2$, NHR, NRR', SR, $CF_3$ or halogen;
$R_2$ and $R_3$ are independently selected from hydrogen, alkyl, alkoxy, hydroxyl, $NH_2$, NHR, NRR', SR, haloalkyl or halogen;
$R_4$ and $R_5$ are independently selected from hydrogen, alkyl, $CH_2NHCOR''$ or $CH_2CONHR''$; and,
$R_6$, $R_7$ and $R_8$ are either all alkyl or all alkoxy;
wherein at least one of the substituents $R_4$ and $R_5$ is an alkyl group; and
wherein R and R' are independently selected from $C_{1-10}$ alkyl groups and R'' is a $C_{1-10}$ alkyl group, aryl group or heteroaryl group;
or a salt, an ester, a free acid or base or a hydrate thereof.

2. The compound of claim 1 which is the cis or Z-isomer.
3. The compound of claim 1 which is the trans or E-isomer.
4. The compound of claim 1, wherein the alkyl group $R_4$ and/or $R_5$ is a methyl or ethyl group.
5. The compound of claim 1, wherein the compound is selected from one of the compounds having said structural formula wherein
(i) $R_1$ represents methoxy, $R_2$, $R_3$ and $R_4$ each represent hydrogen, $R_5$ represents methyl, $R_6$, $R_7$ and $R_8$ each represent methoxy and X represents hydroxy; or (ii) $R_1$ represents methoxy, $R_2$, $R_3$ and $R_4$ each represent hydrogen, $R_5$ represents ethyl, $R_6$, $R_7$ and $R_8$ each represent methoxy and X represents hydroxy.

6. A compound represented by the structural formula:

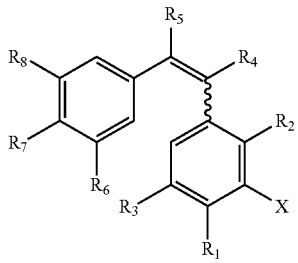

wherein:
the zigzag line indicates that the compound can be cis or trans;
X is selected from hydroxyl, nitro, aryl, heteroaryl, alkyl, alkoxy, CHO, COR, halogen, haloalkyl, $NH_2$, NHR, NRR', SR, $CONH_2$, CONHR, CONHRR', O-aryl, O-heteroaryl or O-ester;
$R_1$ is selected from alkyl, CHO, alkoxy, $NH_2$, NHR, NRR', SR or $CF_3$;
$R_2$ and $R_3$ are independently selected from hydrogen, alkyl, alkoxy, hydroxyl, $NH_2$, NHR, NRR', SR, haloalkyl or halogen;
$R_4$ and $R_5$ are independently selected from hydrogen, alkyl, $CH_2NHCOR''$ or $CH_2CONHR''$; and,
$R_6$, $R_7$ and $R_8$ are all alkyl groups; and
wherein R and R' are independently selected from $C_{1-10}$ alkyl groups and R" is a $C_{1-10}$ alkyl group, aryl group or heteroaryl group;
or a salt, an ester, a free acid or base or a hydrate thereof.

7. The compound of claim 6, wherein the $R_6$, $R_7$ and $R_8$ groups are methyl, ethyl or propyl groups.

8. The compound of claim 6, wherein the compound is selected from one of compounds having said formula wherein
(i) $R_1$ represents methoxy, $R_2$, $R_3$, $R_4$ and $R_5$ each represent hydrogen, $R_6$, $R_7$ and $R_8$ each represent methyl and X represents fluorine; or
(ii) $R_1$ represents methoxy, $R_2$, $R_3$, $R_4$ and $R_5$ each represent hydrogen, $R_6$, $R_7$ and $R_8$ each represent methyl and X represents hydroxy.

9. A compound represented by the structural formula:

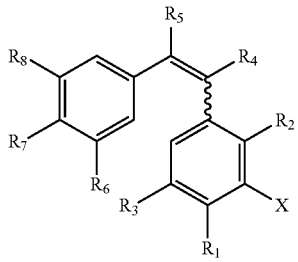

wherein:
the zigzag line indicates that the compound can be cis or trans;
$R_1$ is selected from alkyl, alkoxy, $NH_2$, NHR, NRR', SR, $CF_3$, CHO or halogen;

$R_2$ and $R_3$ are independently selected from hydrogen, alkyl, alkoxy, hydroxyl, $NH_2$, NHR, NRR', SR, haloalkyl or halogen;
$R_4$ and $R_5$ are independently selected from hydrogen, alkyl, $CH_2NHCOR''$ or $CH_2CONHR''$; and,
$R_6$, $R_7$ and $R_8$ are independently selected from hydrogen, alkyl or alkoxy; and,
wherein R and R' are independently selected from substituted or unsubstituted $C_{1-10}$ alkyl groups and R" is a substituted or unsubstituted $C_{1-10}$ alkyl group, aryl group or heteroaryl group;
or a salt thereof;
wherein X is a group represented by:

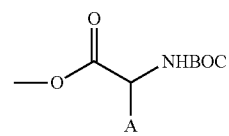

wherein BOC represents a t-butoxycarbonyl group and the A group is a naturally occurring amino acid side chain.

10. The compound of claim 9, wherein the BOC amino acid ester comprises Phe, Ile, Gly, Trp, Met, Leu, Ala, His, Pro, D-Met, D-Trp, or Tyr.

11. The compound of claim 9, wherein the amino acid is Phe, the A group is —$CH_2Ph$.

12. A composition comprising the compound of claim 1 and a pharmaceutically acceptable carrier.

13. A composition comprising the compound of claim 6 and a pharmaceutically acceptable carrier.

14. A composition comprising the compound of claim 9 and a pharmaceutically acceptable carrier.

15. A method for the treatment of cancer or a condition characterized by abnormal proliferation of the vasculature in a patient in need of said treatment by administering a therapeutically effective amount of a compound of claim 1.

16. The method of claim 15, wherein said compound is administered for treatment of a condition characterized by abnormal proliferation of the vasculature that is selected from the group of diabetic retinopathy, psoriasis and endometriosis.

17. A method for treatment of cancer or a condition characterized by abnormal proliferation of the vasculature in a patient in need of said treatment by administering a therapeutically effective amount of a compound of claim 6.

18. The method of claim 17, wherein said compound is administered for treatment of a condition characterized by abnormal proliferation of the vasculature that is selected from the group of diabetic retinopathy, psoriasis and endometriosis.

19. A method for the treatment of cancer or a condition characterized by abnormal proliferation of the vasculature in a patient in need of said treatment by administering a therapeutically effective amount of a compound of claim 9.

20. The method of claim 19, wherein said compound is administered for treatment of a condition characterized by abnormal proliferation of the vasculature that is selected from the group of diabetic retinopathy, psoriasis and endometriosis.